(12) United States Patent
Kim et al.

(10) Patent No.: US 10,167,391 B2
(45) Date of Patent: Jan. 1, 2019

(54) AZO COMPOUND, USE THEREOF AND METHOD FOR PREPARING SAME

(71) Applicant: BIONEER CORPORATION, Daejeon (KR)

(72) Inventors: Sun Gi Kim, Daejeon (KR); Taewoo Kwon, Daejeon (KR); Jung Yung Choi, Daejeon (KR)

(73) Assignee: BIONEER CORPORATION, Daejeon (KR)

(*) Notice: Subject to any disclaimer, the term of this patent is extended or adjusted under 35 U.S.C. 154(b) by 749 days.

(21) Appl. No.: 14/417,510

(22) PCT Filed: Aug. 2, 2013

(86) PCT No.: PCT/KR2013/006998
§ 371 (c)(1),
(2) Date: Jan. 26, 2015

(87) PCT Pub. No.: WO2014/021680
PCT Pub. Date: Feb. 6, 2014

(65) Prior Publication Data
US 2017/0016050 A1    Jan. 19, 2017

(30) Foreign Application Priority Data

Aug. 2, 2012  (KR) .................. 10-2012-0084754
Aug. 2, 2013  (KR) .................. 10-2013-0091821

(51) Int. Cl.
| C09B 31/14 | (2006.01) |
| C07D 213/72 | (2006.01) |
| C07D 277/82 | (2006.01) |
| C09B 31/153 | (2006.01) |
| C12Q 1/6818 | (2018.01) |

(52) U.S. Cl.
CPC ............ *C09B 31/14* (2013.01); *C07D 213/72* (2013.01); *C07D 277/82* (2013.01); *C09B 31/153* (2013.01); *C12Q 1/6818* (2013.01)

(58) Field of Classification Search
CPC .............................. C09B 31/14; C12Q 1/6818
USPC .......................................... 546/26.6; 435/6.1
See application file for complete search history.

(56) References Cited

U.S. PATENT DOCUMENTS

| 3,096,140 A | 7/1963 | Gaetani |
| 4,394,070 A | 7/1983 | Brown et al. |
| 6,756,488 B2 | 6/2004 | Mikoshiba et al. |
| 7,504,495 B2 | 3/2009 | Lomholt et al. |
| 7,960,543 B2 | 6/2011 | Hirao et al. |
| 2009/0299041 A1 | 12/2009 | Laikhter et al. |
| 2010/0182543 A1 | 6/2010 | Goto et al. |
| 2011/0177315 A1 | 7/2011 | Iwahashi et al. |

FOREIGN PATENT DOCUMENTS

| GB | 961213 A | 6/1964 |
| JP | S58-21451 A | 2/1983 |
| JP | 05-86006 A | 4/1993 |
| JP | H08-108625 A | 4/1996 |
| JP | 2004-001375 A | 1/2004 |
| JP | 2010-106242 A | 5/2010 |
| JP | 2011-150162 A | 8/2011 |
| JP | 2012-057046 A | 3/2012 |
| WO | 0186001 A1 | 11/2001 |
| WO | 02072865 A2 | 9/2002 |
| WO | 02099141 A1 | 12/2002 |
| WO | 2004022578 A2 | 3/2004 |
| WO | 2005049849 A2 | 6/2005 |
| WO | 2006084067 A2 | 8/2006 |
| WO | WO 2006132588 | * 12/2006 |
| WO | 2009019115 A1 | 2/2009 |
| WO | 2010-106242 A | 5/2010 |
| WO | 2011024890 A1 | 3/2011 |
| WO | 2011024892 A1 | 3/2011 |

OTHER PUBLICATIONS

Szadowski et al. (Przeglad Wiokienniczy 1988, 42(10) 436-9 (abstract).*
Fengxian et al. Dyes and Pigments (2008), 77(3), 564-569 (abstract).*
Lakowicz, J., "Principles of fluorescence spectroscopy, 2nd Edition", pp. 1-698, Publisher: Kluwer Academic/Plenum Publishers, Published in: New York, New York/United States of America.
Note: For the non-patent literature citations that no month of publication is indicated, the year of publication is moe than 1 year prior to the effective filing date of the present application.
Buzzoni, V., et al., "Aza-Boronic Acids as Non-Beta-Lactam Inhibitors of AmpC-Beta-Lactamase", "Bioorganic & Medicinal Chemistry Letters", Jun. 19, 2004, pp. 3979-3983, vol. 14.
Cognard, J., et al., "The Use of Azo Dyes in Guest-Host Displays", "Molecular Crystals and Liquid Crystals", 1981, pp. 207-229, vol. 68, Publisher: Gordon and Breach, Science Publishers, Inc.
Kiprianov, A.I., et al., "Cyamin Dyes with Two Conjugated Chromophores", "Soviet Progress in Chemistry", 1968, pp. 795-799, vol. 34, No. 8, Publisher: Allerton Press.
Ning, Z., et al., "Synthetis and Characterization of Several Bisazobenzenes", Dec. 2008.
Peters, A.T., et al., "Disazo Disperse Dyes Derived from 5,6(6,7)-Dichloro-2-AminobenzothiazoleD", "Dyes and Pigments", Jun. 1996, pp. 131-139, vol. 31, No. 2, Publisher: Elsevier Applied Science Publishers.

(Continued)

*Primary Examiner* — Jezia Riley

(74) *Attorney, Agent, or Firm* — Hultquist, PLLC; Steven J. Hultquist

(57) ABSTRACT

The present invention provides a novel azo compound having a quenching ability for the material that exhibits a luminescent phenomenon at an excited energy level, a quencher comprising the novel azo compound, a use of the quencher and a method for preparing the azo compound. The quencher according to the present invention may exhibit excellent characteristics in a wavelength absorption region.

15 Claims, 3 Drawing Sheets

(56) References Cited

OTHER PUBLICATIONS

Seki, H., et al, "Light-Stability of Guest-Host Cells", "Molecular Crystals and Liquid Crystals", 1981, pp. 209-218, vol. 66, Publisher: Gordon and Breach Science Publishers, Inc.
Sogomonova, R., et al., "The Simplest Arenes as Azo Components", "Journal of Organic Chemistry of the USSR=Zhurnal Organicheskoi Khimi, M A I K Nauka—Interperiodica, RU", Jan. 1, 1980, pp. 2008-2013, vol. 16.
Uchida, T., et al., "Guest-Host Interactions in Nematic Liquid Crystal Cells with Twisted and Tilted Alignments", "Molecular Crystals and Liquid Crystals", Mar. 22, 1979, pp. 161-174, vol. 54.

\* cited by examiner

AZO COMPOUND, USE THEREOF AND METHOD FOR PREPARING SAME

CROSS-REFERENCE TO RELATED APPLICATIONS

This application is a U.S. national phase under the provisions of 35 U.S.C. § 371 of International Patent Application No. PCT/KR13/06998 filed Aug. 2, 2013, which in turn claims priority of Korean Patent Application No. 10-2012-0084754 filed Aug. 2, 2012 and Korean Patent Application No. 10-2013-0091821 filed Aug. 2, 2013. The disclosures of such international patent application and both Korea priority patent applications are hereby incorporated herein by reference in their respective entireties, for all purposes.

TECHNICAL FIELD

The present invention relates to a novel azo compound, a novel quencher comprising the azo compound, the use of the quencher, and a method for preparing the azo compound.

BACKGROUND ART

Fluorescence resonance energy transfer (FRET) quenching is a phenomenon in which an energy donor, a reporter excited by light, transfers its energy to an energy acceptor that is a quencher neighboring thereto (J. R. Lakowicz, Principles of fluorescence spectroscopy, 1999, Kluwer Academic/Plenum Publishers, New York). Herein, the efficiency of energy transfer has a close relation with the distance between the reporter and the quencher, is inversely proportional to the sixth power of the distance between the reporter and the quencher. Thus, if the distance between the two is longer than a certain distance, fluorescence resonance energy transfer (FRET) quenching will not occur.

In an example of fluorescence resonance energy transfer quenching, if a TAMRA fluorophore is used as the energy acceptor (quencher), light energy from the energy donor is absorbed into the absorption region of the energy acceptor. The absorbed energy becomes an excited state and is emitted in the emission region of the energy acceptor.

The energy transfer process in this quenching phenomenon occurs even when the quencher is composed of an azo compound. However, light emission from the quencher that is the energy acceptor does not occur. A quencher such as an azo compound in this transfer process differs from the above TAMRA fluorophore in that it emits energy in place of light by the action of heat or other agent. This quencher such as an azo compound is called "dark quencher". The dark quencher emits heat energy in place of light energy during energy transfer, and thus a dye having no fluorescence. A fluorescent quencher can increase background noise, because the fluorescence spectra of the quencher and the reporter can overlap. However, the dark quencher provides a solution to this disadvantage, because it has no fluorescence, and thus causes no noise. In addition, the dark quencher provides an advantage in that two or more reporter-quencher probes can be used.

Representative compounds having a dark quencher structure BHQ1, BHQ2 and BHQ3, which are BHQ quencher derivatives (WO2001/086001A1). These quenchers comprise a diazo bond between dialkylaniline acting as an electron donor and an aromatic compound acting as an electron acceptor, and absorb fluorescence in a wavelength region of about 500-700 nm. However, a quencher having a salt structure is unstable during oligomer synthesis and purification, and an example thereof is BHQ3.

Other examples may include BBQ quencher (WO2006/084067A2) and quinone-based Iowa black quencher (U.S. Pat. No. 7,504,495B2). However, these quenchers have poor wavelength absorption ability compared to the above-described BHQ quenchers.

Meanwhile, quenchers are linked with fluorophores and used mainly in the chemical or biological field. In order to detect a target molecule, protein or nucleic acid, a molecule capable of binding complementarily thereto, a quencher and a fluorophore may be linked with one another, and the emission of fluorescence therefrom may be measured to determine whether the target material is present. This plays a great role in advanced development in the chemical and biological fields. A representative example of the application of the fluorescence resonance energy transfer theory in the biological field is the use of probes in real-time polymerase chain reaction (RT-PCR). The probes are used to detect specific regions of nucleotide sequences, and have recently been frequently used in real-time polymerase chain reaction (RT-PCR).

Examples of the probes include a TaqMan probe, a molecular beacon probe and the like. The TaqMan probe is a probe comprising a reporter (energy donor) attached to one end and a quencher attached to the other end. During polymerase chain reaction, the reporter escapes the influence of the quencher and emits its characteristic fluorescence. The level of fluorescence increases in proportion to the progression of polymerase chain reaction. The level of fluorescence is quantified and used as an indirect measure. The molecular beacon probe is hairpin-shaped and composed of a stem and a loop. When the molecular beacon probe is attached to a specific region during polymerase chain reaction, the structure is disassembled, and the reporter escapes the influence of the quencher, and emits its fluorescence.

The quencher can explain energy transfer from the reporter in the probe based on the quenching phenomenon of the fluorescence resonance energy transfer theory. Thus, the relationship between the reporter and the quencher in the probe plays an important role in the performance of the probe. If the quencher absorbs fluorescence in a broad wavelength region from the reporter linked to the probe, the limitation of fluorophores that can be used will be eliminated, and an excellent probe that can easily achieves detection can be fabricated. In other words, if the quencher absorbs fluorescence in a broader wavelength range, it may be linked with various fluorescent dyes to prepare probes.

Accordingly, the present inventors have made extensive efforts to develop a quencher having a higher efficiency, and as a result, have found that a quencher comprising a novel azo compound has excellent quenching properties, thereby completing the present invention.

DISCLOSURE OF INVENTION

It is an object of the present invention to provide a novel azo compound and a novel quencher comprising the azo compound.

Another object of the present invention is to provide an oligonucleotide comprising the quencher.

Still another object of the present invention is to provide a novel azo compound and a method for preparing the novel azo compound.

To achieve the above objects, the present invention provides a quencher comprising a compound represented by the following formula 1:

$$A^1-N=N-A^2-N=N-A^3 \quad \quad \text{Formula 1}$$

wherein

A$^1$ has a structure of the following formula 2 or 3;

A$^2$ is a substituted or unsubstituted C$_6$-C$_{12}$ arylene group, or a substituted or unsubstituted C$_4$-C$_{12}$ heteroarylene group; and A$^3$ is a substituted or unsubstituted C$_6$-C$_{30}$ aryl group, or a substituted or unsubstituted C$_3$-C$_{30}$ heteroaryl group, Formula 2

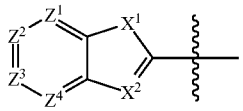

wherein

Z$^1$ to Z$^4$ are each independently CR$^1$ or nitrogen;

R$^1$ is hydrogen, a halogen, a C$_1$-C$_{10}$ alkoxy group, a nitro group, a cyano group or a sulfonyl group;

X$^1$ is CH$_2$, NH, sulfur or oxygen; and

X$^2$ is CH or nitrogen,

Formula 3

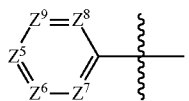

wherein

Z$^5$ to Z$^9$ are each independently CR$^2$ or nitrogen;

R$^2$ is hydrogen, a hydroxyl group, a C$_1$-C$_{10}$ alkoxy group, NR$^9$R$^{10}$, a C$_1$-C$_{10}$ alkyl group, a C$_1$-C$_{10}$ carboxyl group, or a halogen; and R$^9$ and R$^{10}$ are each independently hydrogen or a C$_1$-C$_{10}$ alkyl group.

A$^2$ in formula 1 preferably has a structure of the following formula 4:

Formula 4

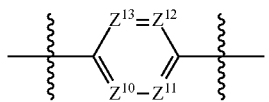

wherein

Z$^{10}$ to Z$^{13}$ are each independently CR$^3$ or nitrogen;

R$^3$ is hydrogen, a hydroxyl group, a C$_1$-C$_{10}$ alkoxy group, NR$^{11}$R$^{12}$, a C$_1$-C$_{10}$ alkyl group, a C$_1$-C$_{10}$ carboxyl group, a C$_6$-C$_{30}$ aryloxy group, or a halogen; and R$^{11}$ and R$^{12}$ are each independently hydrogen or a C$_1$-C$_{10}$ alkyl group.

Also, A$^3$ in formula 1 preferably has a structure of the following formula 5:

Formula 5

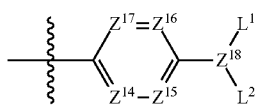

wherein,

Z$^{14}$ to Z$^{17}$ are each independently CR$^4$ or nitrogen;

R$^4$ is hydrogen, a hydroxyl group, a C$_1$-C$_{10}$ alkoxy group, NR$^{13}$R$^{14}$, a C$_1$-C$_{10}$ alkyl group, a C$_1$-C$_{10}$ carboxyl group, or a halogen;

R$^{13}$ and R$^{14}$ are each independently hydrogen or a C$_1$-C$_{10}$ alkyl group;

Z$^{18}$ is CH or nitrogen; and

L$^1$ and L$^2$ are each independently hydrogen, a C$_1$-C$_{30}$ alkyl group, a C$_6$-C$_{30}$ aryl group, a hydroxy-substituted C$_1$-C$_{30}$ alkyl group, a C$_6$-C$_{30}$ aryl-substituted C$_1$-C$_{30}$ alkyl group, a C$_1$-C$_{30}$ carboxyl group, a C$_1$-C$_{30}$ carbonyloxy-substituted C$_1$-C$_{30}$ alkyl group, or a C$_3$-C$_{30}$ heteroaryl group.

The present invention also provides an oligonucleotide comprising the quencher.

In addition, the present invention provides a novel azo compound, and a method for preparing the azo compound, the method comprising sequentially performing a first azo coupling reaction and a second coupling reaction on aniline.

ADVANTAGEOUS EFFECTS

A quencher comprising a novel azo compound according to the present invention has a strong and broad absorption region, and thus quenches fluorescence in a broader wavelength compared to conventional quenchers. Thus, the quencher of the present invention enables the use of various fluorophores as energy donors. Also, the quencher of the present invention is stable during oligomer synthesis and purification. It can be used in various applications in the biological and chemical fields.

In addition, a method for preparing an azo composition according to the present invention can overcome the limitation of conventional methods, and can easily synthesize an azo compound containing three or more heterocyclic rings, unlike conventional methods.

BEST MODE FOR CARRYING OUT THE INVENTION

Figure 1:
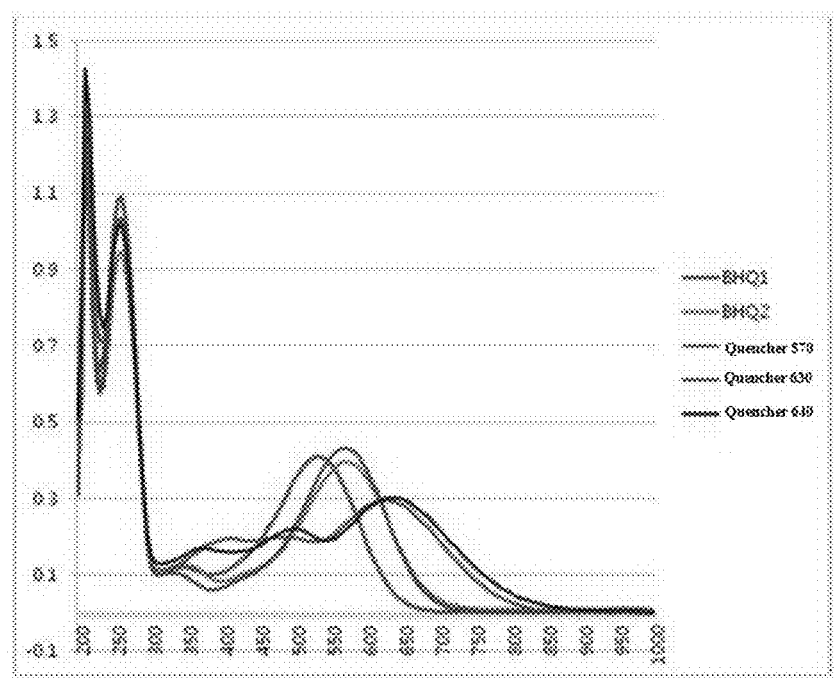
FIG. 1 is a graph showing the emission intensities of various quenchers.
Figure 2:
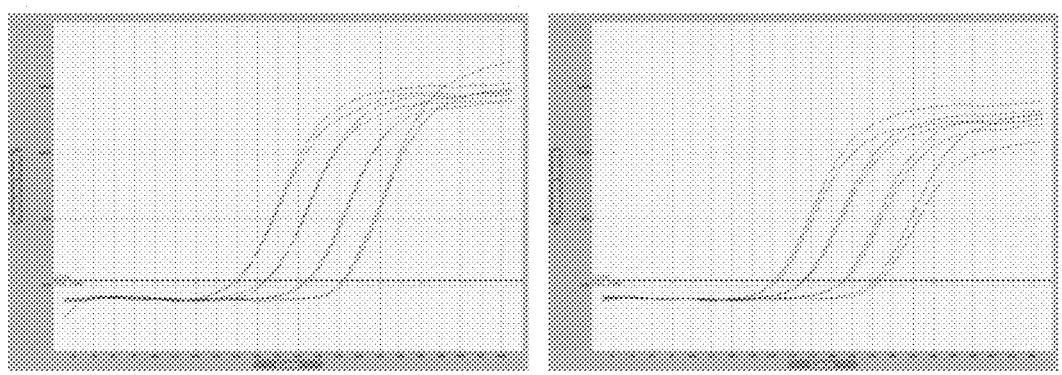
FIG. 2 is a graph showing the results of measuring fluorescence intensity (y-axis) as a function of the number of cycles (x-axis) in real-time (RT)-PCR using probes comprising FAM as a fluorophore and each of quencher 570 (invention) and BHQ1 as a quencher.
Figure 3:
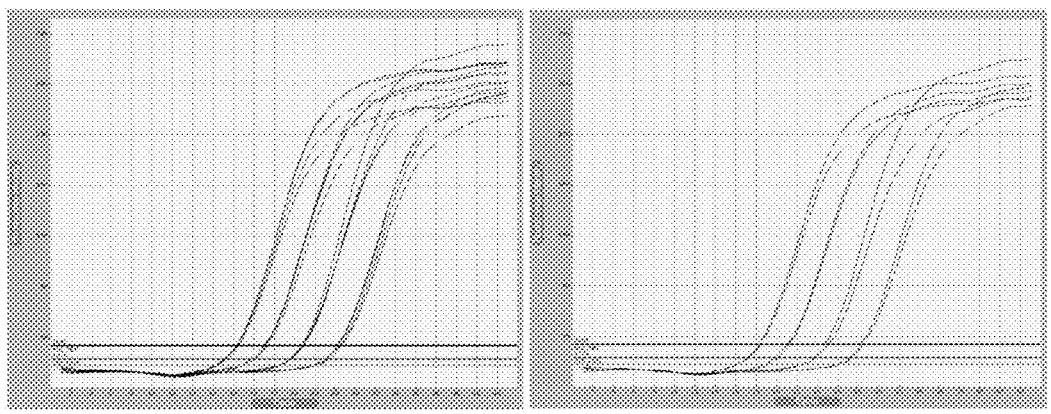
FIG. 3 is a graph showing the results of measuring fluorescence intensity (y-axis) as a function of the number of cycles (x-axis) in real-time (RT)-PCR using probes comprising TET as a fluorophore and each of quencher 570 (invention) and BHQ1 as a quencher.
Figure 4:
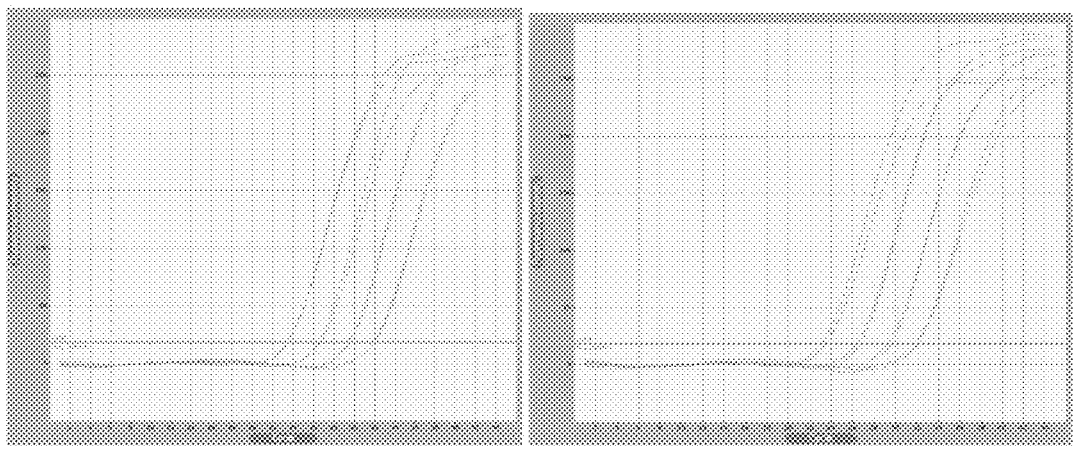
FIG. 4 is a graph showing the results of measuring fluorescence intensity (y-axis) as a function of the number of cycles (x-axis) in real-time (RT)-PCR using probes comprising TAMRA as a fluorophore and each of quencher 570 (invention) and BHQ1 as a quencher.
Figure 5:
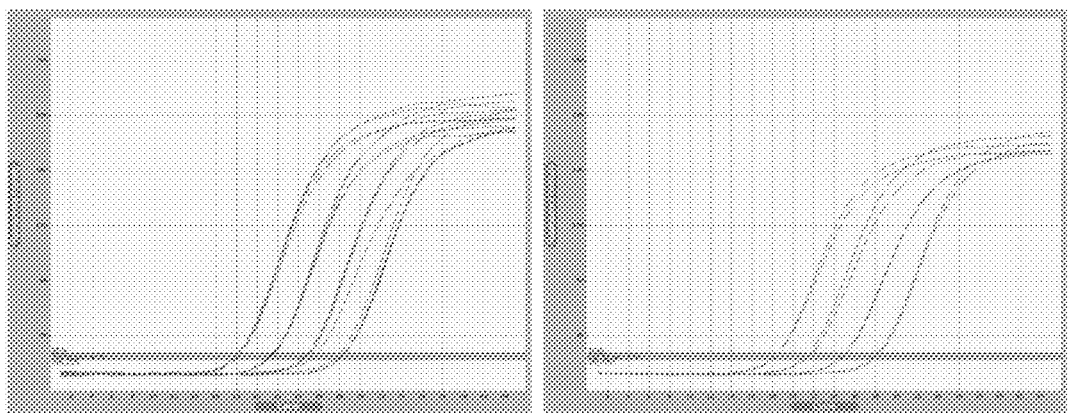
FIG. 5 is a graph showing the results of measuring fluorescence intensity (y-axis) as a function of the number of cycles (x-axis) in real-time (RT)-PCR using probes comprising ROX as a fluorophore and each of quencher 570 (invention) and BHQ2 as a quencher.
Figure 6:
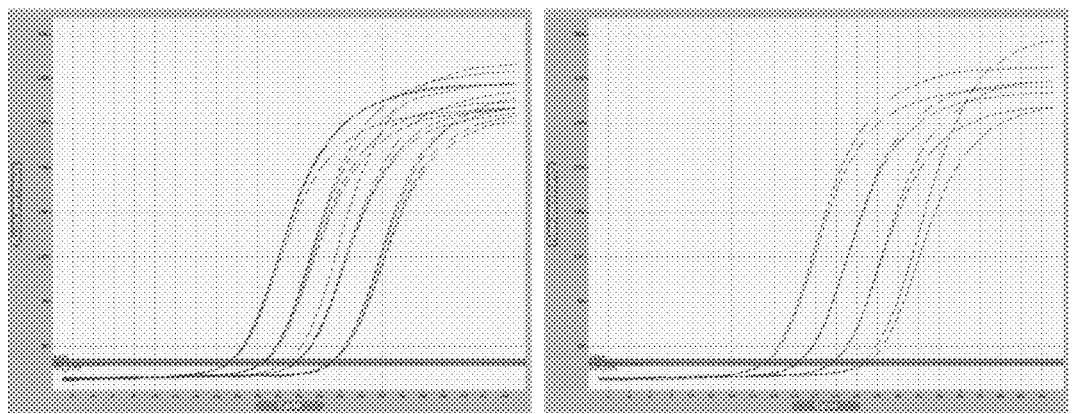
FIG. 6 is a graph showing the results of measuring fluorescence intensity (y-axis) as a function of the number of cycles (x-axis) in real-time (RT)-PCR using probes comprising Texas-Red as a fluorophore and each of quencher 570 (invention) and BHQ2 as a quencher.

Hereinafter, the present invention will be described in detail.

In one aspect, the present invention is directed to a quencher comprising a compound represented by the following formula 1:

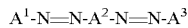   Formula 1 wherein $A^1$ has a structure of the following formula 2 or 3;

$A^2$ is a substituted or unsubstituted $C_6$-$C_{12}$ arylene group, or a substituted or unsubstituted $C_4$-$C_{12}$ heteroarylene group; and $A^3$ is a substituted or unsubstituted $C_6$-$C_{30}$ aryl group, or a substituted or unsubstituted $C_3$-$C_{30}$ heteroaryl group,

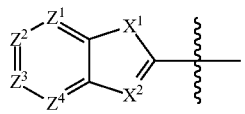   Formula 2 wherein $Z^1$ to $Z^4$ are each independently $CR^1$ or nitrogen;

$R^1$ is hydrogen, a halogen, a $C_1$-$C_{10}$ alkoxy group, a nitro group, a cyano group or a sulfonyl group;

$X^1$ is $CH_2$, NH, sulfur or oxygen; and $X^2$ is CH or nitrogen,

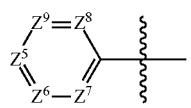   Formula 3 wherein $Z^5$ to $Z^9$ are each independently $CR^2$ or nitrogen;

$R^2$ is hydrogen, a hydroxyl group, a $C_1$-$C_{10}$ alkoxy group, $NR^9R^{10}$, a $C_1$-$C_{10}$ alkyl group, a $C_1$-$C_{10}$ carboxyl group, or a halogen; and $R^9$ and $R^{10}$ are each independently hydrogen or a $C_1$-$C_{10}$ alkyl group.

As used herein, the term "substituted" means that an unsubstituted substituent is substituted with one or more selected from the group consisting of deuterium, halogens, ($C_1$-$C_{30}$)alkyl, halogen-substituted ($C_1$-$C_{30}$)alkyl, ($C_6$-$C_{30}$)aryl, ($C_3$-$C_{30}$)heteroaryl, ($C_6$-$C_{30}$)aryl-substituted ($C_5$-$C_{30}$)heteroaryl, ($C_3$-$C_{30}$)cycloalkyl, heterocycloalkyl, tri($C_1$-$C_{30}$)alkylsilyl, tri($C_6$-$C_{30}$)arylsilyl, di($C_1$-$C_{30}$)alkyl ($C_6$-$C_{30}$)arylsilyl, ($C_1$-$C_{30}$)alkyldi($C_6$-$C_{30}$)arylsilyl, ($C_2$-$C_{30}$)alkenyl, ($C_2$-$C_{30}$)alkynyl, cyano, carbazolyl, di($C_1$-$C_{30}$)alkylamino, di($C_6$-$C_{30}$)arylamino, ($C_1$-$C_{30}$)alkyl($C_6$-$C_{30}$)arylamino, di($C_6$-$C_{30}$)arylboronyl, di($C_1$-$C_{30}$)alkylboronyl, ($C_1$-$C_{30}$)alkyl($C_6$-$C_{30}$)arylboronyl, ($C_6$-$C_{30}$)ar($C_1$-$C_{30}$)alkyl, ($C_1$-$C_{30}$)alkyl($C_6$-$C_{30}$)aryl, ($C_1$-$C_{30}$)alkyloxy, ($C_6$-$C_{30}$)aryloxy, carboxyl, nitro, and hydroxy.

$A^2$ in formula 1 preferably has a structure of the following formula 4:

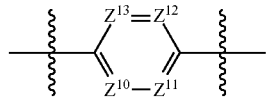   Formula 4 wherein $Z^{10}$ to $Z^{13}$ are each independently $CR^3$ or nitrogen;

$R^3$ is hydrogen, a hydroxyl group, a $C_1$-$C_{10}$ alkoxy group, $NR^{11}R^{12}$, a $C_1$-$C_{10}$ alkyl group, a $C_1$-$C_{10}$ carboxyl group, a $C_6$-$C_{30}$ aryloxy group, or a halogen; and $R^{11}$ and $R^{12}$ are each independently hydrogen or a $C_1$-$C_{10}$ alkyl group.

$A^3$ in formula 1 preferably has a structure of the following formula 5:

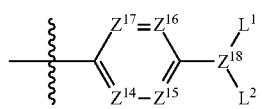   Formula 5 wherein, $Z^{14}$ to $Z^{17}$ are each independently $CR^4$ or nitrogen;

$R^4$ is hydrogen, a hydroxyl group, a $C_1$-$C_{10}$ alkoxy group, $NR^{13}R^{14}$, a $C_1$-$C_{10}$ alkyl group, a $C_1$-$C_{10}$ carboxyl group, or a halogen;

$R^{13}$ and $R^{14}$ are each independently hydrogen or a $C_1$-$C_{10}$ alkyl group;

$Z^{18}$ is CH or nitrogen; and $L^1$ and $L^2$ are each independently hydrogen, a $C_1$-$C_{30}$ alkyl group, a $C_6$-$C_{30}$ aryl group, a hydroxy-substituted $C_1$-$C_{30}$ alkyl group, a $C_6$-$C_{30}$ aryl-substituted $C_1$-$C_{30}$ alkyl group, a $C_1$-$C_{30}$ carboxyl group, a $C_1$-$C_{30}$ carbonyloxy-substituted $C_1$-$C_{30}$ alkyl group, or a $C_3$-$C_{30}$ heteroaryl group.

A quencher comprising $A^3$ represented by formula 5 may further comprise a cleavable support linked by any one linker selected from among L1 and L2. Also, the quencher may further comprise a hydroxyl group protected with DMT (4,4'-dimethoxytrityl group) or its derivative as a protecting group.

The support is a solid material that helps a nucleic acid or a polypeptide to be linked with the quencher. It functions to fix the 3' end of the quencher in linkage with an oligomer to facilitate the synthesis of oligomer chains. The support is intended to include resin, solid supports, solid phase materials and the like, which perform the same function. The support may be composed of polystyrene, polyethylene, polypropylene, polyfluoroethylene, polyethyleneoxy, polyacrylamide, or a copolymer of two or more thereof. Also, it may be composed of glass, silica, CPG, or reverse-phase silica. Preferably, it may be made of CPG (controlled pore glass) or polystyrene.

The linker that is used in the present invention functions mainly to link the quencher to other materials, and those having this function may all be used as the linker in the present invention. An example of the linker in the present invention may be 1 to 6 ethylene glycol moieties or carbon chains, but is not limited thereto. This linker has little or no effect on reactive functionality or fluorescence and quenching properties.

In addition, the reactive functional group in the quencher may be protected with at least one protecting group selected from the group consisting of DMT (dimethoxytrityl group), MMT (monomethoxytrityl group), a trityl group, a substituted trityl group, a pixyl group, and a trialkylsilyl group. Among them, DMT is preferred. The hydroxyl group in the present invention can be bound by DMT. For oligomer synthesis, DMT can be removed, and then a desired oligomer can be synthesized.

The compound represented by formula 1 may preferably be a compound selected from compounds represented by the following formulas 6 and 7, but is not limited thereto:

Formula 6

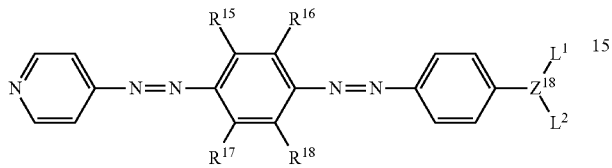

Formula 7

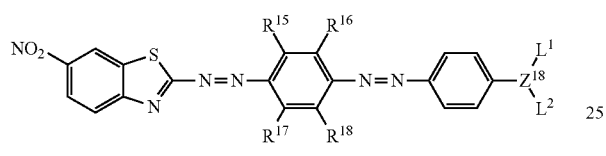

wherein $Z^{18}$ is CH or nitrogen;

$L^1$ and $L^2$ are each independently hydrogen, a $C_1$-$C_{30}$ alkyl group, a $C_6$-$C_{30}$ aryl group, a hydroxy-substituted $C_1$-$C_{30}$ alkyl group, a $C_6$-$C_{30}$ aryl-substituted $C_1$-$C_{30}$ alkyl group, a $C_1$-$C_{30}$ carboxyl group, a $C_1$-$C_{30}$ carbonyloxy-substituted $C_1$-$C_{30}$ alkyl group, or a $C_3$-$C_{30}$ heteroaryl group; and $R^{15}$ to $R^{18}$ are each independently H, a $C_1$-$C_{10}$ alkoxy group, or a $C_1$-$C_{10}$ alkyl group.

More preferably, the compound represented by formula 1 may be any one selected from among compounds represented by the following formulas 8 to 12, but is not limited thereto:

Formula 8

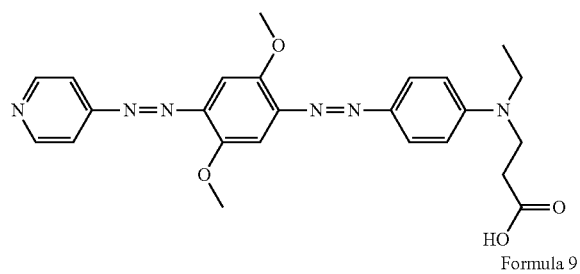

Formula 9

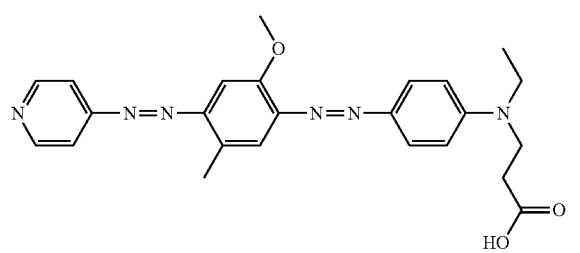

Formula 10

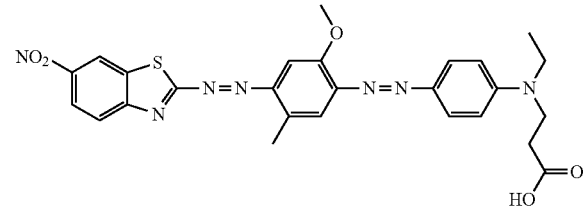

Formula 11

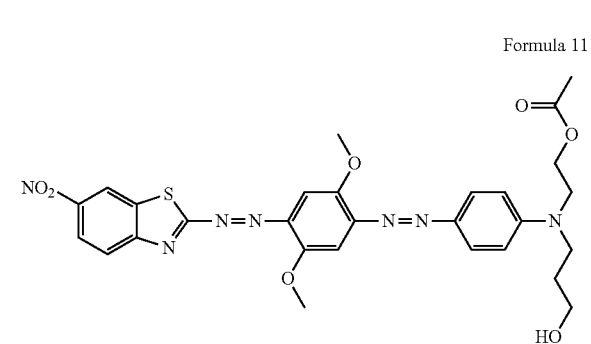

Formula 12

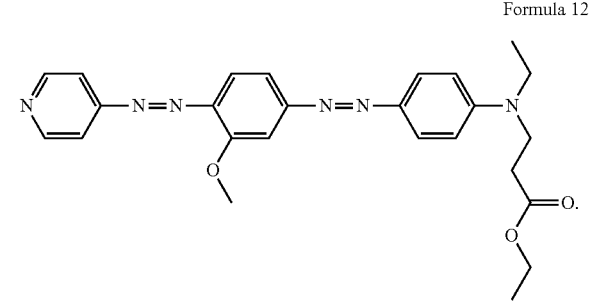

A quencher comprising any one of the compounds represented by formulas 8 to 12 may further comprise a linker and a support for oligomer synthesis. Herein, the linker may be linked by amination of a carboxyl group (see Preparation Examples). The support is preferably CPG (controlled pore glass) or polystyrene, and more preferably CPG.

In addition, the quencher may further comprise a functional group. This functional group is selected from those that do not affect the functions of the reporter and the quencher. The functional group enables the quencher to be more efficiently linked with an oligomer. Thus, the functional group of the quencher, which can react with an oligomer for oligomer synthesis, can be protected with DMT or its derivative, and the quencher may comprise an intermediate that is linked with the support.

More preferably, the quencher according to the present invention further comprises any one selected from among compounds represented by the following formulas 13 to 17 for oligomer synthesis:

Formula 13

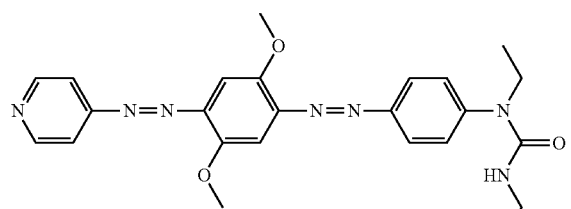

Formula 14

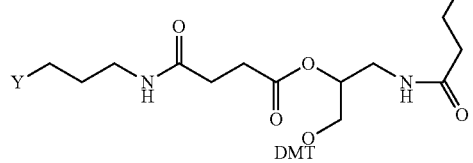

Formula 15

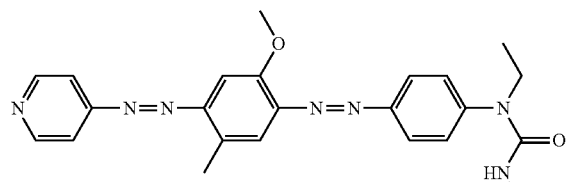

Formula 16

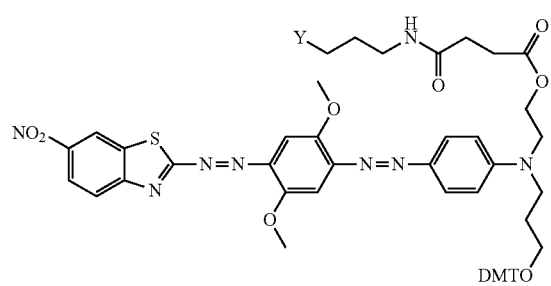

Formula 17

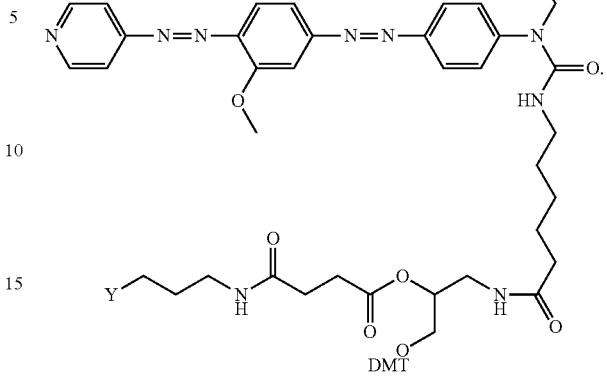

In formulas 13 to 17, Y is a support, and may be selected from CPG (controlled pore glass) or polystyrene. CPG is preferred.

The supports in the quenchers comprising the compounds of formulas 13 to 17 are linked to the compounds of formulas 8 to 12, respectively, by the linkers and the hydroxyl group is protected with DMT. Immediately before linkage with a reaction-specific oligomer, an oligomer can be synthesized. The synthesized oligomer can be linked with the quencher and used in various chemical and biological studies.

In the present invention, quenchers having the structures of formulas 13 to 17 were named "quencher 570", "quencher 545", "quencher 630", "quencher 640", and "quencher 530", respectively. 'quencher000' used in the following examples and the drawings indicates the quencher of the present invention.

In an example of the present invention, the emission intensities of quencher 570, quencher 630, quencher 640, and conventional quenchers BHQ1 and BHQ2 were measured, and as a result, it was shown that the quenchers of the present invention can absorb fluorescence in a broader wavelength range compared to the conventional quencher BHQ (see FIG. 1). Particularly, quencher 570 has the ability to absorb fluorescence in a broader wavelength range compared to a conventional single quencher, and thus quencher 570 alone can absorb fluorescence in the wavelength range of conventional BHQ1 and BHQ2. This indicates that the quencher according to the present invention is an energy acceptor that absorbs fluorescence from a fluorophore, and has a strong and broad absorption region due to the efficient arrangement of an electron donor and an electron acceptor, and thus can efficiently function as a quencher.

In another aspect, the present invention is directed to an oligonucleotide comprising the quencher. The quencher of the present invention can bind to a oligonucleotide so that it can be used in biological or chemical analysis. For the purpose of analysis, the oligonucleotide can be suitably modified.

The term "oligonucleotide" means a polymer consisting of one to several hundred nucleotides, and is intended to include DNA, RNA or PNA. Also, the oligonucleotide is intended to include its derivatives, for example, those that can be easily modified by those skilled in the art, such as those having a chemically modified nucleotide, or those having sugar bound thereto. In addition, the oligonucleotide is intended to include single-stranded or double-stranded oligonucleotides.

The oligonucleotide preferably comprises a probe. This probe is preferably a probe that can bind complementarily to a target nucleic acid, but is not limited thereto.

The probe may be selected from among nucleic acids, peptides, saccharides, oligonucleotides, proteins, antibodies, and combinations thereof, but is not limited thereto.

The probe preferably comprises a fluorophore. The fluorophore that is contained in the probe may include one or more selected from the group consisting of coumarin, fluorescein, rhodamine, BODIPY, cyanine, and derivatives thereof. In addition, because the quencher according to the present invention absorbs fluorescence in a broad wavelength range, it enables the use of various fluorophores as reporters, and a fluorophore that may be used in the present invention is not limited to the above-described fluorophores.

This oligonucleotide may be used in various applications in the chemical and biological fields. Particularly, it can be advantageously used in real-time polymerase chain reactions or microassays, but is not limited thereto.

Therefore, the present invention is directed to a composition for detecting a nucleic acid, comprising the oligonucleotide. The composition comprises an oligonucleotide capable of binding complementarily to a target nucleic acid, and thus can specifically detect the target nucleic acid. In addition, the composition may further comprise a component that can be easily selected by those skilled in the art and that can be contained in conventional detection compositions.

The present invention is also directed to a method for detecting a nucleic acid or a protein using the above-described probe. This method comprises the steps of: brining the probe into contact with a sample having a target substance; and analyzing fluorescence.

The present invention is also directed to an azo compound selected from compounds represented by the following formulas 6 and 7:

Formula 6

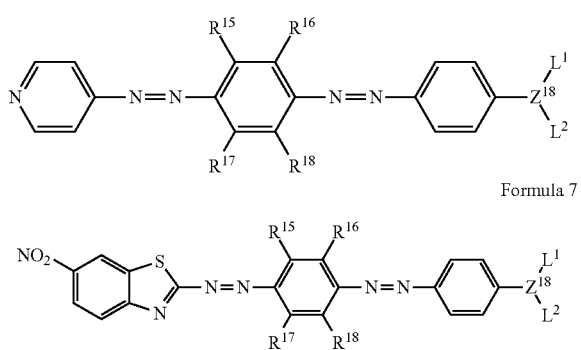

Formula 7 wherein $Z^{18}$ is CH or nitrogen;

$L^1$ and $L^2$ are each independently hydrogen, a $C_1$-$C_{30}$ alkyl group, a $C_6$-$C_{30}$ aryl group, a hydroxy-substituted $C_1$-$C_{30}$ alkyl group, a $C_6$-$C_{30}$ aryl-substituted $C_1$-$C_{30}$ alkyl group, a $C_1$-$C_{30}$ carboxyl group, a $C_1$-$C_{30}$ carbonyloxy-substituted $C_1$-$C_{30}$ alkyl group, or a $C_3$-$C_{30}$ heteroaryl group; and $R^{15}$ to $R^{18}$ are each independently H, a $C_1$-$C_{10}$ alkoxy group, or a $C_1$-$C_{10}$ alkyl group.

The present invention is also directed to a method for preparing an azo compound containing three or more heterocyclic rings. Specifically, the present invention provides methods for preparing an azo compound selected from azo compounds represented by the following formulas 6 and 7.

The method for preparing the azo compound represented by the following formula 6 according to the present invention comprises the steps of:

subjecting an aniline of the following formula 6a to an azo coupling reaction with a compound of the following formula 6b to obtain a compound of the following formula 6c; and subjecting the obtained compound of formula 6c to an azo coupling reaction with a compound of the following formula 6d to obtain a compound of formula 6:

Formula 6a

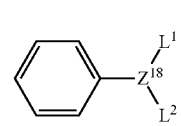

Formula 6b

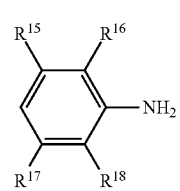

Formula 6c

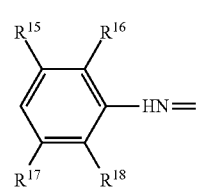

Formula 6d

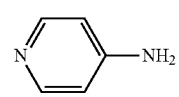

Formula 6

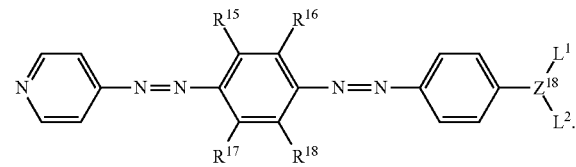

wherein $Z^{18}$ is CH or nitrogen;

$L^1$ and $L^2$ are each independently hydrogen, a $C_1$-$C_{30}$ alkyl group, a $C_6$-$C_{30}$ aryl group, a hydroxy-substituted $C_1$-$C_{30}$ alkyl group, a $C_6$-$C_{30}$ aryl-substituted $C_1$-$C_{30}$ alkyl group, a $C_1$-$C_{30}$ carboxyl group, a $C_1$-$C_{30}$ carbonyloxy-substituted $C_1$-$C_{30}$ alkyl group, or a $C_3$-$C_{30}$ heteroaryl group; and $R^{15}$ to $R^{18}$ are each independently H, a $C_1$-$C_{10}$ alkoxy group, or a $C_1$-$C_{10}$ alkyl group.

Also, the method for preparing the azo compound represented by the following formula 7 according to the present invention comprises the steps of:

obtaining the compound of formula 6c; and subjecting the obtained compound of formula 6c to an azo coupling reaction with a compound of the following formula 7a to obtain a compound of the following formula 7:

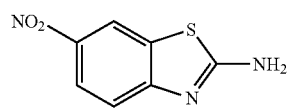

Formula 7a

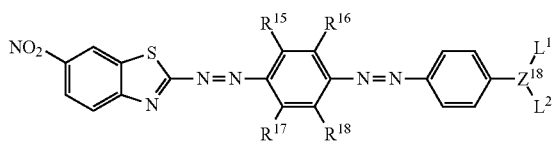

Formula 7 wherein $Z^{18}$ is CH or nitrogen;

$L^1$ and $L^2$ are each independently hydrogen, a $C_1$-$C_{30}$ alkyl group, a $C_6$-$C_{30}$ aryl group, a hydroxy-substituted $C_1$-$C_{30}$ alkyl group, a $C_6$-$C_{30}$ aryl-substituted $C_1$-$C_{30}$ alkyl group, a $C_1$-$C_{30}$ carboxyl group, a $C_1$-$C_{30}$ carbonyloxy-substituted $C_1$-$C_{30}$ alkyl group, or a $C_3$-$C_{30}$ heteroaryl group; and $R^{15}$ to $R^{18}$ are each independently H, a $C_1$-$C_{10}$ alkoxy group, or a $C_1$-$C_{10}$ alkyl group.

In the prior art, it was not easy to form an azo compound containing three or more heterocyclic rings, and thus examples that specifically disclose an azo compound containing three or more heterocyclic rings were rare.

The method for preparing the azo compound according to the present invention is characterized by synthesizing an azo compound containing three or more heterocyclic rings. According to the present invention, there is provided a method for preparing an azo compound containing three or more heterocyclic rings, in which a first azo coupling reaction is performed on aniline that is a starting compound, followed by a second azo coupling reaction.

A known method comprises linking two heterocyclic compounds to each other, and linking the two kinked heterocyclic compounds to aniline by an azo coupling reaction. This known method is not easy in substantial synthesis.

Thus, the present invention provides a method capable of easily synthesizing an azo compound containing three or more heterocyclic rings. The method for preparing the azo compound according to the present invention is characterized by sequentially performing two coupling reactions.

In the prior art, a synthesis method that uses an electron withdrawing group (EWG) was reported. However, when a strong electron withdrawing group is introduced, reactivity for second coupling significantly decreases, and thus second coupling is difficult to proceed. Thus, in a process of synthesizing a quencher compound by azo coupling, if an azo compound synthesized by first azo coupling has a strong electron withdrawing group, the basicity of the first azo compound is reduced due to the strong electron withdrawing action of the electron withdrawing group. For this reason, a second azo coupling reaction is difficult to proceed. To solve this, in the method for preparing the azo compound according to the present invention, the first azo coupling reaction is performed with a compound having an electron donating group. In order to make the production of azonium salt predominant in a competitive reaction between ammonium salt and azonium salt, the control of reaction rate and the choice of a suitable solvent should be taken into consideration. Then, second azo coupling with a compound having a strong electron withdrawing group is performed. In order to maximize the reactivity of first and second coupling reactions, reaction conditions such as temperature, solvent, pH and the like should be efficiently controlled. To overcome the above-described limitation, synthesis is started with an electron donating group, and an electron withdrawing group is introduced in second azo coupling, whereby a quencher having a strong electron withdrawing group can be synthesized.

Hereinafter, the present invention will be described in further detail with reference to preparation examples and examples. It is to be understood, however, that these examples are for illustrative purposes only and are not intended to limit the scope of the present invention. Unless otherwise defined, all terms used herein, including technical or scientific terms, have the same meanings as understood by those skilled in the technical field to which the present invention pertains.

PREPARATION EXAMPLE 1

Preparation of Compound of Formula 13 (Quencher 570)

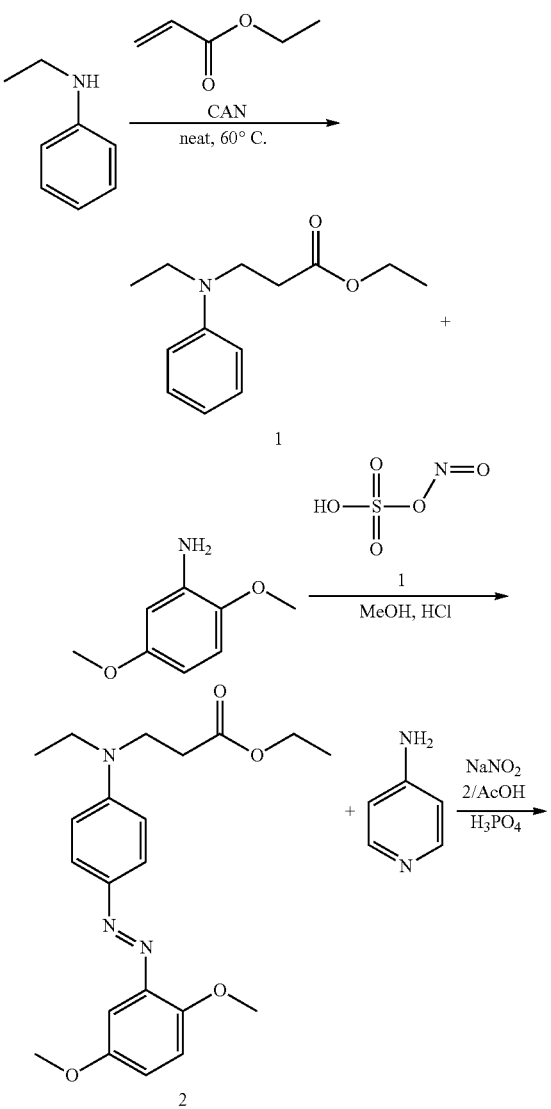

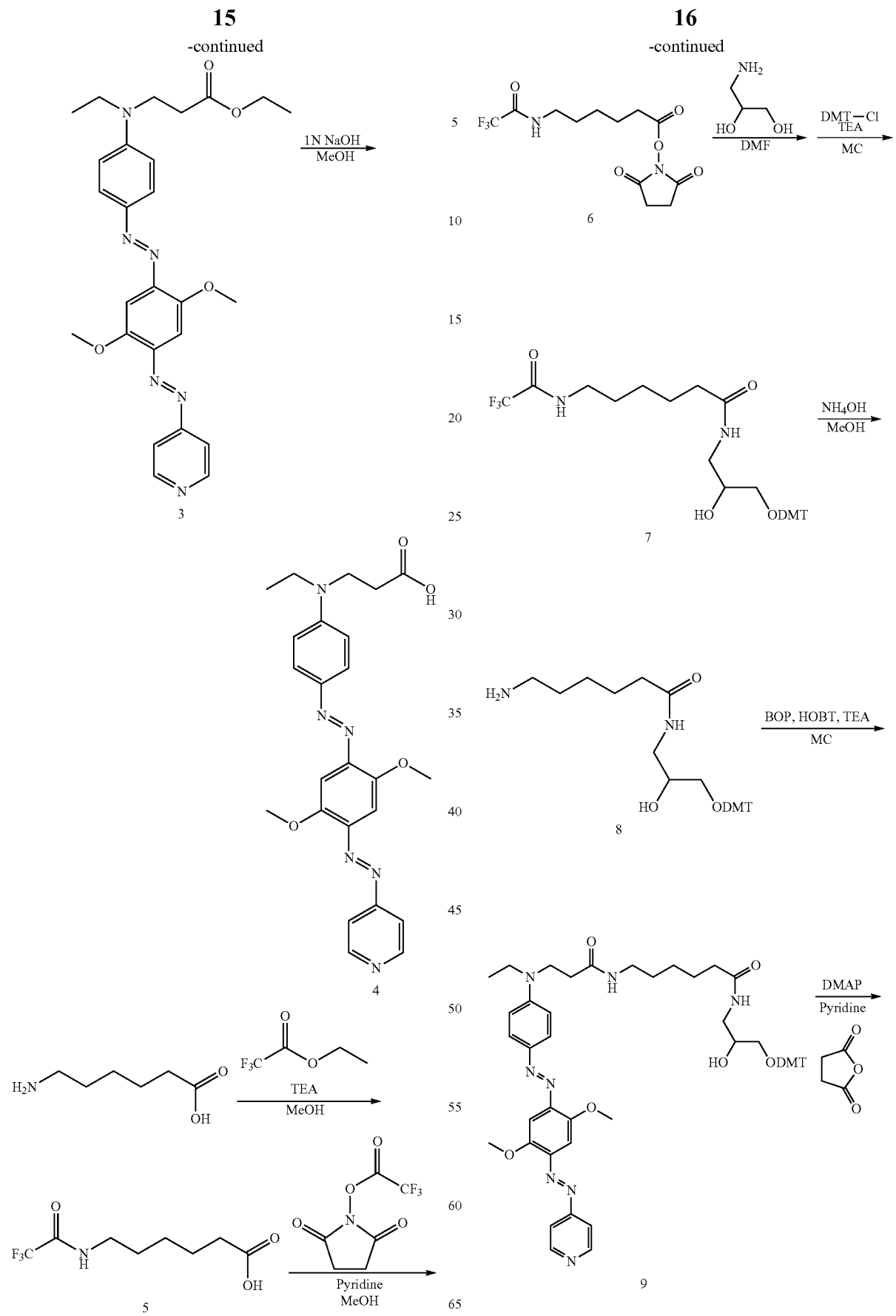

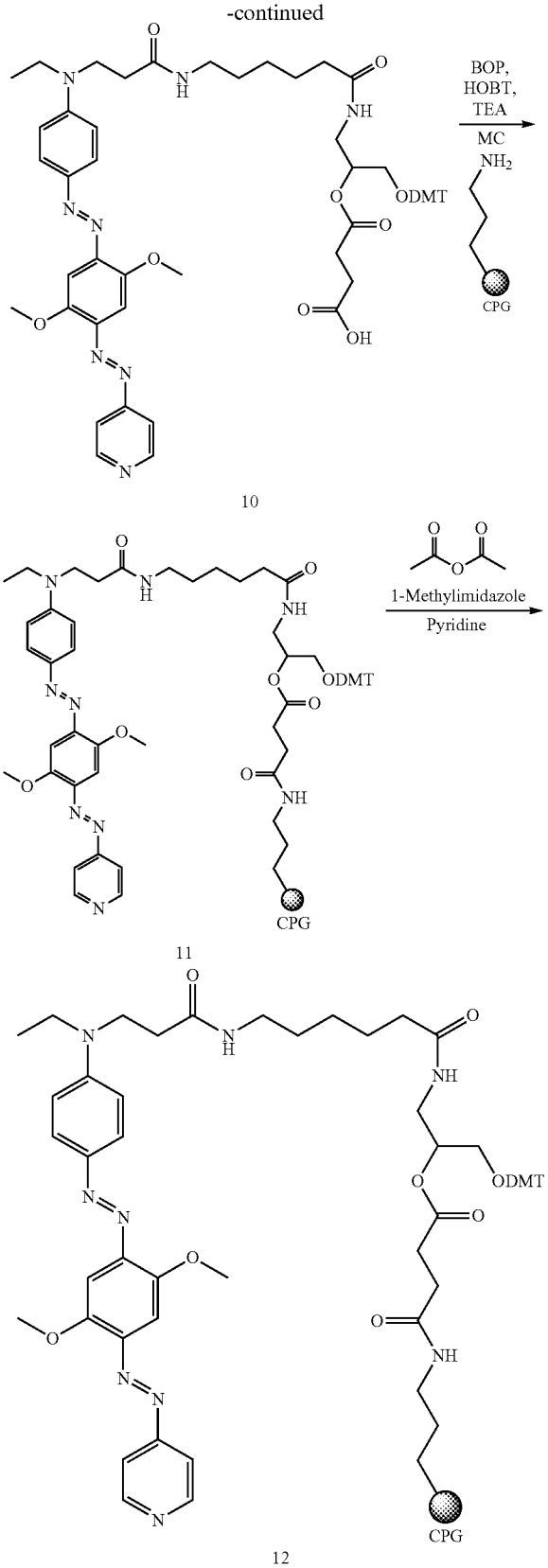

eq) of cerium (IV) ammonium nitrate were mixed and stirred. Then, the mixture was heated to 60° C. and stirred for 15 hours. The reaction mixture was cooled to room temperature and extracted with methylene chloride. The extract dried with sodium sulfate and filtered. The filtrate was concentrated under reduced pressure and separated by a column. The separated product was concentrated under reduced pressure and dried in a vacuum to afford 47 g of the desired compound (yellow liquid, 85.8%).

$^1$H NMR (300 MHz, CDCl$_3$): 7.27-7.20 ppm (2H, t), 6.73-6.67 ppm (3H, m),4.20-4.11 ppm (2H, q), 3.67-3.61 ppm (2H, t), 3.43-3.35 ppm (2H, q), 2.63-2.57 ppm (2H, t), 1.31-1.24 ppm (3H, t), 1.19-1.14 ppm (3H, t)

1-2: Preparation of Compound of Process 2—First Azo Coupling 10.37 g (32.64 mmol, 1 eq) of nitrosylsulfuric acid, 50 ml of hydrochloric acid and 150 ml of methanol were mixed and stirred. Then, the mixture was cooled to −78° C. and stirred for 20 minutes. Then, a solution of 5 g (32.64 mmol, 1 eq) of 2,5-methoxyaniline in 100 ml of methanol was added dropwise to the reaction mixture, which was then heated to room temperature and stirred for 2 hours.

A solution of 7.95 g (35.91 mmol, 1.1 eq) of the process 1 compound in methanol was added dropwise thereto, followed by stirring for 1 hour. Then, the reaction solution was neutralized with a saturated aqueous solution of sodium hydrocarbonate to a pH of 6-8. The neutralized solution was stirred for 15 hours. Then, the solution was concentrated under reduced pressure to remove methanol. The residue was extracted with methylene chloride and filtered. The filtrate was concentrated under reduced pressure and separated by a column. The separated material was concentrated under reduced pressure and dried in a vacuum to afford 5.87 g of the desired compound (orange liquid, 46.7%).

$^1$H NMR (300 MHz, CDCl$_3$): 7.90-7.86 ppm (2H, d), 7.27-7.25 ppm (1H, s), 7.01-6.93 ppm (2H, m), 6.75-6.72 ppm (2H, d), 4.20-4.12 ppm (2H, q), 3.99-3.97 ppm (3H, s), 3.84-3.82 ppm (3H, s), 3.75-3.69 ppm (2H, t), 3.50-3.44 ppm (2H, q), 2.67-2.61 ppm (2H, t), 1.30-1.18 ppm (6H, m)

1-3: Preparation of Compound of Process 3—Second Azo Coupling 1.05 g (15.23 mmol, 1 eq) of sodium nitrate and 150 ml of phosphoric acid were mixed and stirred. Then, the solution was cooled to 0° C. and stirred for 20 minutes. 1.43 g (15.23 mmol, 1 eq) of 4-aminopyridine was added thereto, followed by stirring at room temperature for 30 minutes. A solution of 5.87 g (15.23 mmol, 1 eq) of the process 2 compound in 50 ml of acetic acid was added dropwise thereto, followed by stirring for 1 hour. The reaction solution was added to 200 ml of distilled water, neutralized with a saturated aqueous solution of sodium hydrocarbonate to a pH of 4-8, and then stirred for 15 hours. Then, the reaction solution was extracted with methylene chloride. The extract was dried with sodium sulfate and filtered. The filtrate was concentrated under reduced pressure and separated by a column.

The separated material was concentrated under reduced pressure and dried in a vacuum to afford 1.6 g of the desired compound (dark purple solid, 21.4%).

$^1$H NMR (300 MHz, CDCl$_3$): 8.81-8.78 ppm (2H, d), 7.96-7.92 ppm (2H, d), 7.74-7.71 ppm (2H, d), 7.50-7.48 ppm (1H, s), 7.47-7.45 ppm (1H, s), 6.77-6.74 ppm (2H, d), 4.22-4.14 ppm (2H, q), 4.10-4.08 ppm (3H, s), 4.06-4.04 ppm (3H, s), 3.79-3.73 ppm (2H, t), 3.54-3.48 ppm (2H, q), 2.70-2.64 ppm (2H, t), 1.31-1.21 ppm (6H, m)

1-1: Preparation of Compound of Process 1—Amination 30 g (250 mmol, 1 eq) of N-ethylaniline, 37.2 g (370 mmol, 1.5 eq) of ethyl acrylate and 13.57 g (25 mmol, 0.1

1-4. Preparation of Compound of Process 4—Hydrolysis 1.49 g (3.04 mmol, 1 eq) of the process 3 compound, 200 ml of methanol and 200 ml of methylene chloride were mixed and stirred. 9.11 ml (9.11 mmol, 3 eq) of 1N sodium hydroxide was added thereto, followed by stirring for 3 days. Then, 3.04 ml (3.04 mmol, 1 eq) of 1N sodium hydroxide was added to the reaction solution, which was then stirred for 1 day and concentrated under reduced pressure. 400 ml of distilled water was added thereto, followed by stirring. Then, the reaction solution was neutralized with 1N hydrochloric acid to a pH of 6-8, followed by extraction with methylene chloride. The extract was dried with sodium sulfate, dried and filtered. The filtrate was concentrated under reduced pressure and dried in a vacuum to afford 1.9 g of the desired compound (dark purple solid).

$^1$H NMR (300 MHz, CDCl$_3$): 8.77-8.74 ppm (2H, d), 7.93-7.89 ppm (2H, d), 7.76-7.73 ppm (2H, d), 7.47-7.45 ppm (1H, s), 7.45-7.43 ppm (1H, s), 6.80-6.76 ppm (2H, d), 4.09-4.07 ppm (3H, s), 4.05-4.03 ppm (3H, s), 3.83-3.77 ppm (2H, t), 3.59-3.51 ppm (2H, q), 2.76-2.70 ppm (2H, t), 1.29-1.23 ppm (3H, t)

1-5: Preparation of Compound of Process 5—Amine Protection 10 g (76.2 mmol, 1 eq) of 6-aminocapric acid, 31.8 ml (228.6 mmol, 3 eq) of triethylamine and 76 ml of methanol were mixed and stirred. 11.9 g (83.76 mmol, 1.1 eq) of ethyl trifluoroacetate was added to the mixture, followed by stirring for 15 hours. Then, the reaction solution was concentrated under reduced pressure and extracted with ethyl acetate. The organic layer was dried with magnesium sulfate, dried and filtered. The filtrate was concentrated under reduced pressure and dried in a vacuum to afford 16.9 g (98.0%) of the desired compound.

$^1$H NMR (300 MHz, DMSO-d$_6$): 11.97-11.95 ppm (1H, s), 9.38-9.36 ppm (1H, s), 3.18-3.10 ppm (2H, q), 2.21-2.14 ppm (2H, t), 1.53-1.41 ppm (4H, m), 1.29-1.18 ppm (2H, m)

1-6: Preparation of Compound of Process 6—NHS Esterification 5.28 g (23.24 mmol, 1 eq) of the process 5 compound, 120 ml of methanol and 9.38 ml (116.2 mmol, 5 eq) of pyridine were mixed and stirred. 8.81 g (41.83 mmol, 1.8 eq) of N-succinimidyl trifluoroacetate was added thereto, followed by stirring for 1 day. The reaction solution was concentrated under the reduced pressure and extracted with methylene chloride. The organic layer was dried with magnesium sulfate, dried and filtered. The filtrate was concentrated under reduced pressure and dried in a vacuum to afford 7.08 g of the desired compound (white solid, 94.8%).

$^1$H NMR (300 MHz, CDCl$_3$): 6.80-6.78 ppm (1H, s), 3.40-3.32 ppm (2H, q), 2.84-2.82 ppm (4H, s), 2.64-2.58 ppm (2H, t), 1.83-1.73 ppm (2H, m), 1.67-1.57 ppm (2H, m), 1.52-1.44 ppm (2H, m)

1-7: Preparation of Compound of Process 7—Amidation (C$_6$-spacer) and DMT Addition 1 g (3 mmol, 1.2 eq) of the process 6 compound, 5 ml of dimethylformamide and 0.23 g (2.57 mmol, 1 eq) of 3-amino-1,2-propanediol were mixed and stirred for 1 hour. 50 ml of methylene chloride was added thereto, followed by cooling to 0° C. 1.13 g (3.33 mmol, 1.3 eq) of diethyl chloride was added thereto, followed by stirring. A dilution of 0.84 ml (6.05 mmol, 2.4 eq) of triethylamine in 10 ml of methylene chloride was added dropwise to the reaction solution, followed by stirring at room temperature for 15 hours. Then, the reaction solution was concentrated under reduced pressure and extracted with methylene chloride. The extract was dried with magnesium sulfate and filtered. The filtrate was concentrated under reduced pressure and separated by a column. The separated material was concentrated under reduced pressure and dried in a vacuum to afford 0.98 g of the desired compound (light yellow solid, 64.5%).

$^1$H NMR (300 MHz, CDCl$_3$): 7.42-7.20 ppm (9H, m), 6.84-6.80 ppm (4H, d), 5.87-5.85 ppm (1H, t), 3.94-3.82 ppm (1H, m), 3.79-3.77 ppm (6H, s), 3.59-3.47 ppm (1H, m), 3.37-3.10 ppm (5H, m), 2.12-2.07 ppm (2H, t), 1.64-1.50 ppm (4H, m), 1.35-1.26 ppm (2H, m)

1-8: Preparation of Compound of Process 8—Amine Deprotection 0.98 g (1.62 mmol, 1 eq) of the process 7 compound and 4 ml of methanol were mixed and stirred. 30 ml (213.98 mmol, 132 eq) of ammonia solution (25%) was added dropwise thereto, followed by stirring for 15 hours. The reaction solution was extracted with methylene chloride, and the extract was dried with sodium sulfate and filtered. The filtrate was concentrated under reduced pressure and dried in a vacuum to afford 0.8 g of the desired compound (light yellow solid, 97%).

$^1$H NMR (300 MHz, CDCl$_3$): 7.42-7.14 ppm (9H, m), 6.83-6.79 ppm (4H, d), 6.04-6.02 ppm (1H, t), 3.87-3.79 ppm (1H, m), 3.78-3.76 ppm (6H, s), 3.59-3.50 ppm (1H, m), 3.22-3.07 ppm (3H, m), 2.66-2.60 ppm (2H, t), 2.12-2.06 ppm (2H, t), 1.62-1.52 ppm (2H, m), 1.43-1.35 ppm (2H, m), 1.33-1.25 ppm (2H, m)

1-9: Preparation of Compound of Process 9—Amidation (C$_9$-spacer)

1.9 g (4.11 mmol, 1 eq) of the process 4 compound, 2 g (4.52 mmol, 1.1 eq) of bis-2-oxo-3-oxazolidinylphosphoric chloride, 0.61 g (4.52 mmol, 1.1 eq) of 1-hydroxybenzotriazole, 2.29 g (4.52 mmol, 1.1 eq) of the process 8 compound and 1 L of methylene chloride were mixed and stirred. 2.85 ml (20.54 mmol, 5 eq) of triethylamine was added thereto and stirred for 15 hours. The reaction solution was concentrated under reduced pressure and extracted with ethyl acetate. The organic layer was dried with sodium sulfate and filtered. The filtrate was concentrated under reduced pressure and separated by a column. The separated material was concentrated under reduced pressure and dried in a vacuum to afford 2.1 g of the desired compound (dark purple solid, 53.7%).

$^1$H NMR (300 MHz, CDCl$_3$): 8.82-8.79 ppm (2H, d), 7.93-7.90 ppm (2H, d), 7.74-7.71 ppm (2H, d), 7.49-7.47 ppm (1H, s), 7.46-7.44 ppm (1H, s), 7.44-7.17 ppm (9H, m), 6.83-6.79 ppm (4H, d), 6.76-6.72 ppm (2H, d), 6.02-5.97 ppm (1H, t), 5.90-5.85 ppm (1H, t), 4.08-4.06 ppm (3H, s), 4.04-4.02 ppm (3H, s), 3.88-3.81 ppm (1H, m), 3.81-3.75 ppm (7H, m), 3.58-3.47 ppm (5H, m), 3.28-3.08 ppm (6H, m), 2.52-2.47 ppm (2H, t), 2.11-2.05 ppm (2H, t), 1.62-1.42 ppm (4H, m), 1.34-1.18 ppm (5H, m)

1-10: Preparation of Compound of Process 10—Succinylation 1.97 g (2.07 mmol, 1 eq) of the process 9 compound, 0.62 g (6.22 mmol, 3 eq) of succinic anhydride, 25 mg (0.21 mmol, 0.1 eq) of N,N-dimethylaminopyridine and 80 ml of pyridine were mixed and stirred. The mixture was heated to 60° C. and stirred for 15 hours. 0.62 g (6.22 mmol, 3 eq) of succinic anhydride was added thereto and stirred for 1 day. Then, 25 mg (0.21 mmol, 0.1 eq) of N,N-dimethylaminopyridine was added to the reaction solution, followed by stirring for 1 day. Then, the reaction solution was cooled to room temperature, concentrated under reduced pressure and extracted with methylene chloride. The extract was dried with sodium sulfate and filtered. The filtrate was concentrated under reduced pressure and separated by a column. The separated material was concentrated under reduced pressure and dried in a vacuum to afford 1.76 g of the desired compound (dark purple solid, 80.9%).

$^1$H NMR (300 MHz, CDCl$_3$): 8.76-8.73 ppm (2H, d), 7.92-7.88 ppm (2H, d), 7.73-7.70 ppm (2H, d), 7.48-7.46 ppm (1H, s), 7.43-7.19 ppm (10H, m), 6.83-6.80 ppm (4H, d), 6.74-6.71 ppm (2H, d), 6.50-6.46 ppm (1H, m), 6.43-6.39 ppm (1H, t), 5.24-5.20 ppm (1H, m), 4.08-4.06 ppm (3H, s), 4.04-4.02 ppm (3H, s), 3.89-3.72 ppm (9H, m), 3.57-3.45 ppm (7H, m), 3.37-3.19 ppm (6H, m), 2.58-2.50 ppm (2H, t), 2.18-2.11 ppm (2H, t), 1.69-1.40 ppm (4H, m), 1.32-1.17 ppm (5H, m)

1-11: Preparation of Compound of Process 11—LCAA-CPG Coupling 3 g of LCAA-CPG, 0.44 g (0.418 mmol, 3.5 eq) of the process 10 compound, 0.18 g (0.418 mmol, 3.5 eq) of bis-2-oxo-3-oxazolidinylphosphoric chloride, 0.06 g (0.418 mmol, 3.5 eq) of 1-hydroxybenzotriazole, 35 ml of methylene chloride and 0.29 ml (2.09 mmol, 17.5 eq) of triethylamine were mixed and stirred at room temperature for 1 day. The reaction solution was filtered and washed with methanol. The filtrate was dried in a vacuum to afford 2.9 g of the desired compound (purple solid).

1-12: Preparation of Compound of Process 12—Capping 2.9 g of the process 11 compound, 35 ml of pyridine, 3.59 ml (38 mmol, 91 eq) of acetic anhydride, and 3.03 ml (38 mmol, 91 eq) of 1-methylimidazole were mixed and stirred for 1 day. The reaction solution was filtered and washed with methanol. The filtrate was dried in a vacuum to afford 2.8 g of the desired compound (purple solid).

PREPARATION EXAMPLE 2

Synthesis of Compound 16 (Quencher 640)

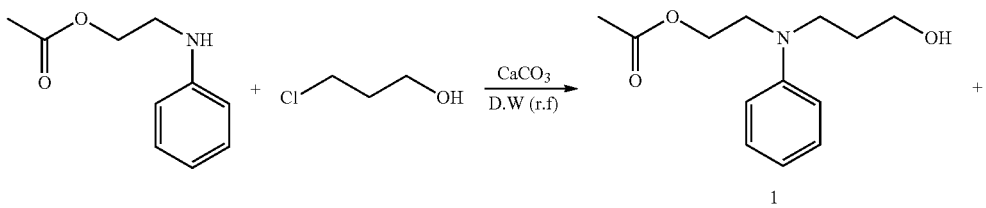

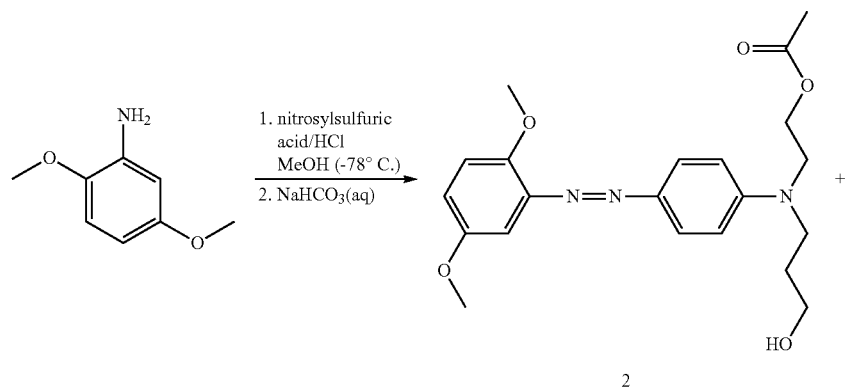

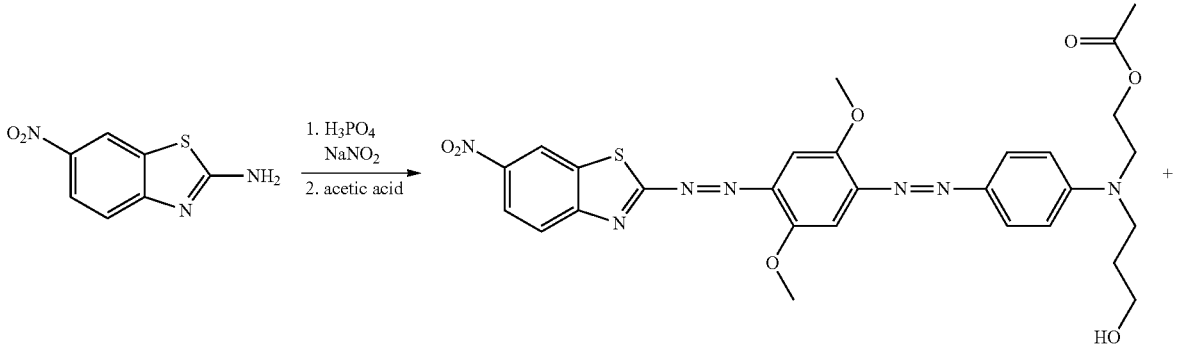

-continued
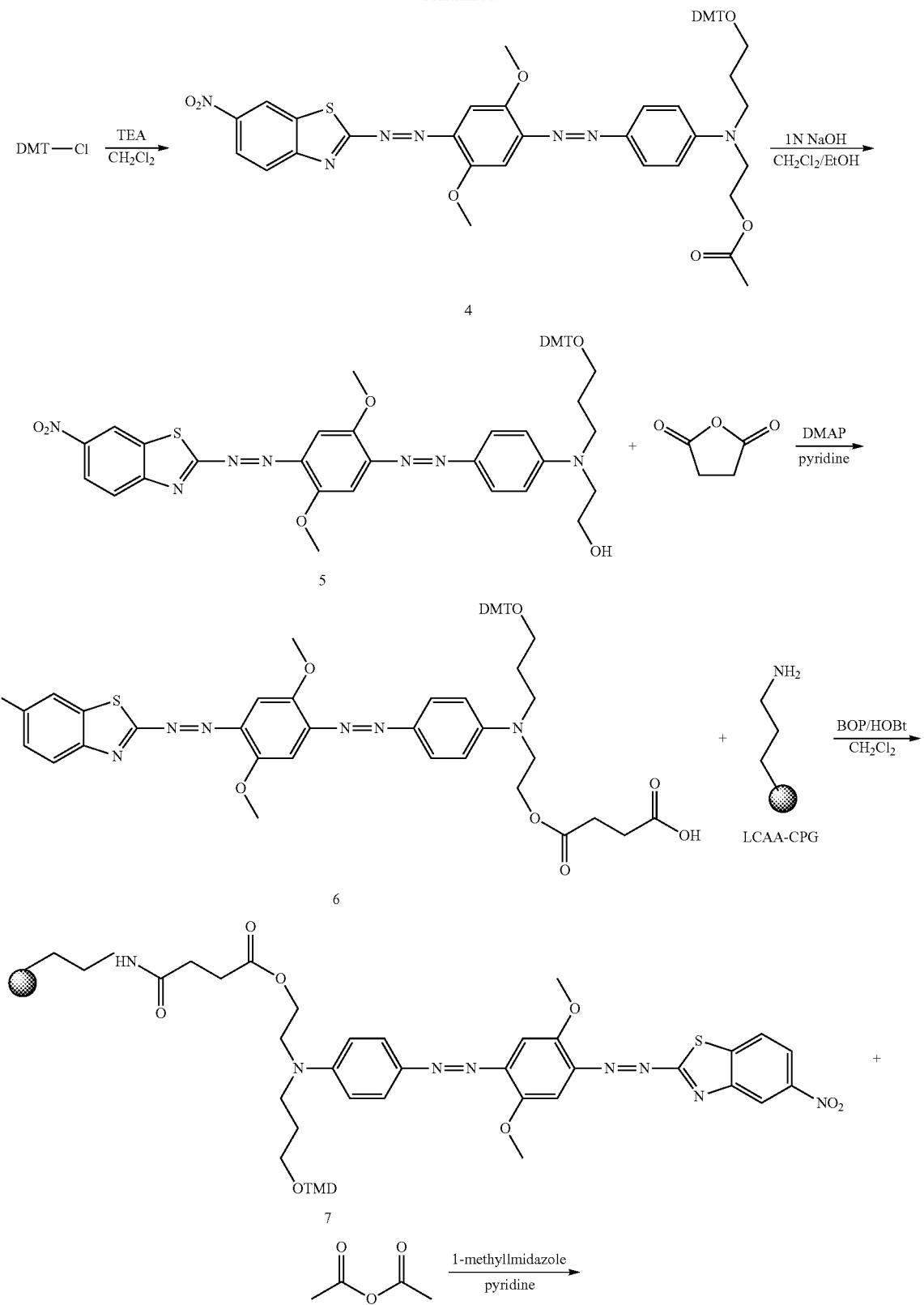

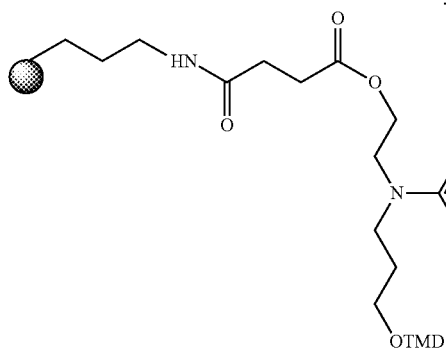 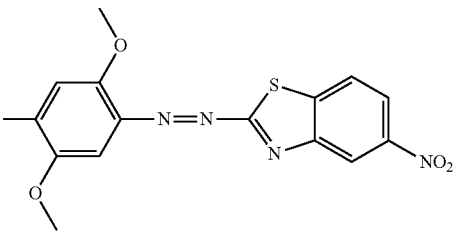

8

2-1: Preparation of Compound of Process 1—Propanol Substitution 12.3 g (68.63 mmol, 1 eq) of N-(2-acetoxyethyl)aniline was added to 40 ml of water, and then 19.86 g (205.90 mmol, 3 eq) of 3-chloro-1-proppanol and 6.87 g (68.63 mmol, 1 eq) of calcium carbonate were added thereto, followed by stirring at 100° C. for 19 hours. Then, the reaction solution was cooled to room temperature and extracted with ethyl acetate. The extract was dried with sodium sulfate and filtered. The filtrate was concentrated under reduced pressure and separated by a column. The separated material was concentrated under reduced pressure to afford 13.8 g of the desired compound (yellow liquid, 84%).

$^1$H NMR (300 MHz, CDCl$_3$): 7.23-7.19 ppm (2H, m), 6.79-6.75 ppm (3H, m), 4.25-4.19 ppm (2H, t), 3.71-3.66 ppm (2H, t), 3.59-3.54 ppm (2H, t), 3.48-3.43 ppm (2H, t), 2.66-2.82 ppm (1H, s, H—OH), 2.05-2.03 ppm (3H, s, H—Ac), 1.90-1.76 ppm (2H, m)

2-2: Preparation of Compound of Process 2—First Azo Coupling 8.4 g (26.12 mmol, 1 eq) of nitrosylsulfuric acid, 4.8 ml (52.24 mmol, 2 eq) of hydrochloric acid and 400 ml of methanol were mixed and stirred. The mixture was cooled to −78° C. and stirred for 20 minutes. Then, a solution of 4 g (26.12 mmol, 1 eq) of 2,5-methoxyaniline in 100 ml of methanol was added dropwise thereto, followed by stirring at room temperature for 2 hours. Then, a solution of 12.5 g (52.24 mmol, 2 eq) of the process 1 compound in methanol was added dropwise to the reaction solution, followed by stirring for 1 hour. Then, the reaction solution was neutralized with a saturated aqueous solution of sodium hydrocarbonate to a pH of 6-8. After completion of neutralization, the reaction solution was stirred for 15 hours and concentrated under reduced pressure to remove methanol. The residue was extracted with methylene chloride and filtered. The filtrate was concentrated under reduced pressure and separated by a column. The separated material was concentrated under reduced pressure and dried in a vacuum to afford 5.6 g of the desired compound (red liquid, 53%).

$^1$H NMR (300 MHz, CDCl$_3$): 7.89-7.85 ppm (2H, d), 7.27-7.25 ppm (1H, d), 7.02-6.92 ppm (2H, m), 6.82-6.78 ppm (2H, d), 4.30-4.25 ppm (2H, t), 3.98-3.97 ppm (3H, s), 3.83-3.82 ppm (3H, s), 3.76-3.66 ppm (4H, m), 3.60-3.55 ppm (2H, t), 2.03-2.02 ppm (3H, s), 1.94-1.87 ppm (2H, m), 1.65-1.64 ppm (1H, s)

2-3: Preparation of Compound of Process 3—Second Azo Coupling 2.3 g (12 mmol, 1 eq) of 2-amino-6-nitro-benzothiazole was added and cooled to 0° C., and then 50 ml of phosphoric acid was added thereto. Then, 0.83 g (12 mmol, 1 eq) of sodium nitrate was added thereto, followed by stirring for 1 hour. Then, a solution of 4.8 g (12 mmol, 1 eq) of the process 2 compound in 30 ml of acetic acid was added dropwise to the reaction solution, followed by cooling to 0° C. Then, the reaction solution was neutralized with a saturated aqueous solution of sodium hydrocarbonate to a pH of 8-9, and then stirred at room temperature for 15 hours. Then, the solid obtained by filtration was added to 600 ml of methanol and boiled for 2 hours. Then, the solution was cooled to room temperature, and the precipitate was filtered. The obtained solid was washed with methanol and dried in a vacuum to afford 3.2 g of the desired compound (brown solid, 44%).

$^1$H NMR (300 MHz, CDCl$_3$): 8.81-8.80 ppm (1H, s), 8.42-8.36 ppm (1H, d), 8.25-8.21 ppm (1H, d), 7.96-7.93 ppm (2H, d), 7.68-7.67 ppm (1H, s), 7.41-7.40 ppm (1H, s), 6.87-6.83 ppm (2H, d), 4.31-4.30 ppm (2H, t), 4.13-4.12 ppm (3H, s), 4.03-4.02 ppm (3H, s), 3.77-3.75 ppm (4H, m), 3.70-3.60 ppm (2H, t), 2.05-2.06 ppm (3H, s), 2.00-1.90 ppm (2H, m)

2-4: Preparation of Compound of Process 4—DMT Protection 2.1 g (3.46 mmol, 1 eq) of the process 3 compound was dissolved in 100 ml of methylene chloride, and then 1.16 g (11.39 mmol) of triethylamine was added thereto. Then, 1.64 g (4.84 mmol) of dimethyl chloride was added thereto, followed by stirring at room temperature for 2 hours. The reaction solution was extracted with methylene chloride. The extract was dried with sodium sulfate and filtered. The filtrate was concentrated under reduced pressure and separated by a column. The separated material was concentrated under reduced pressure to afford 2 g of the desired compound (brown solid, 63%).

$^1$H NMR (300 MHz, CDCl$_3$): 8.76-8.74 ppm (1H, d), 8.34-8.30 ppm(1H, dd), 8.20-8.16 ppm (1H, d), 7.90-7.86 ppm (2H, d), 7.64-7.63 ppm(1H, s), 7.48-7.44 ppm (2H, d), 7.38-7.20 ppm (8H, m), 6.88-6.78 ppm (6H, m), 4.28-4.23 ppm (2H, t), 4.12-4.11 ppm (3H, s), 4.03-4.02 ppm (3H, s), 3.80-3.78 ppm (6H, s), 3.64-3.59 ppm (4H, t), 3.22-3.17 ppm (2H, t), 2.05-2.04 ppm (3H, s), 1.98-1.92 ppm (2H, m)

2-5: Preparation of Compound of Process 5—Hydrolysis 2 g (2.2 mmol, 1 eq) of the process 4 compound, 150 ml of methanol, and 150 ml of methylene chloride were mixed and stirred. 100 ml of 1N sodium hydroxide was added to the mixture, followed by stirring at room temperature for 3 days. The reaction solution was extracted with methylene chloride. The extract was dried with sodium sulfate and filtered.

The filtrate was concentrated under reduced pressure and dried in a vacuum to afford 1.3 g of the desired compound (brown solid, 68%).

$^1$H NMR (300 MHz, CDCl$_3$): 8.74-8.73 ppm (1H, s), 8.33-8.30 ppm (1H, d), 8.18-8.15 ppm (1H, d), 7.87-7.83 ppm (2H, d), 7.62-7.61 ppm (1H, s), 7.43-6.80 ppm (16H, m), 4.09-4.08 ppm (3H, s), 4.00-3.99 ppm (3H, s), 3.78-3.76 ppm (8H, m), 3.61-3.60 ppm (2H, t), 3.53-3.52 ppm (2H, t), 3.17-3.16 ppm (2H, t), 1.92-1.91 ppm (2H, m)

2-6: Preparation of Compound of Process 6—Succinylation 1.3 g (1.50 mmol, 1 eq) of the process 5 compound was completely dissolved in 100 ml of pyridine. 0.018 g (0.15 mmol, 0.1 eq) of N,N-dimethylaminopyridine and 0.5 g (4.50 mmol, 3 eq) of succinic anhydride were added to the solution, followed by stirring at 50° C. for 15 hours. Pyridine was removed using a vacuum pump, and the residue was extracted with methylene chloride. The extract was dried with sodium sulfate and filtered. The filtrate was concentrated under reduced pressure and separated by a column. The separated material was concentrated under reduced pressure to afford 0.85 g of the desired compound (brown solid, 57%).

$^1$H NMR (300 MHz, CDCl$_3$) 8.75-8.74 ppm (1H, s), 8.33-8.30 ppm (1H, d), 8.20-8.16 ppm (1H, d), 7.89-7.85 ppm (2H, d), 7.63-7.60 ppm (1H, s), 7.47-6.70 ppm (16H, m), 4.35-4.27 ppm (2H, t), 4.11-4.10 ppm (3H, s), 4.02-4.01 ppm (3H, s), 3.79-3.78 ppm (6H, s), 3.62-3.61 ppm (4H, m), 3.19-3.18 ppm (2H, t), 2.66-2.60 ppm (4H, m), 1.93-1.92 ppm (2H, m)

2-7: Preparation of Compound of Process 7—LCAA-CPG Coupling 1 g of LCAA-CPG, 0.08 g (0.083 mmol, 2 eq) of the process 6 compound, 0.03 g (0.066 mmol, 1.6 eq) of bis-2-oxo-3-oxazolidinylphosphoric chloride, 0.01 g (0.066 mmol, 1.6 eq) of 1-hydroxybenzotriazole, 10 ml of methylene chloride and 0.042 ml (0.41 mmol, 10 eq) of triethylamine were mixed, and stirred at room temperature for 15 hours. The reaction solution was filtered and washed with methanol. The filtrate was dried in a vacuum to afford 0.8 g of the desired compound (blue solid).

2-8: Preparation of Compound of Process 8—Capping 0.8 g of the process 7 compound, 35 ml of pyridine, 1.23 ml of acetic anhydride and 0.8 ml of 1-methylimidazole were mixed and stirred for 2 hours. The reaction solution was filtered and washed with methanol. The filtrate was dried in a vacuum to afford 0.69 g of the desired compound (blue solid).

PREPARATION EXAMPLE 3

Preparation of Compound 15 (Quencher 630)

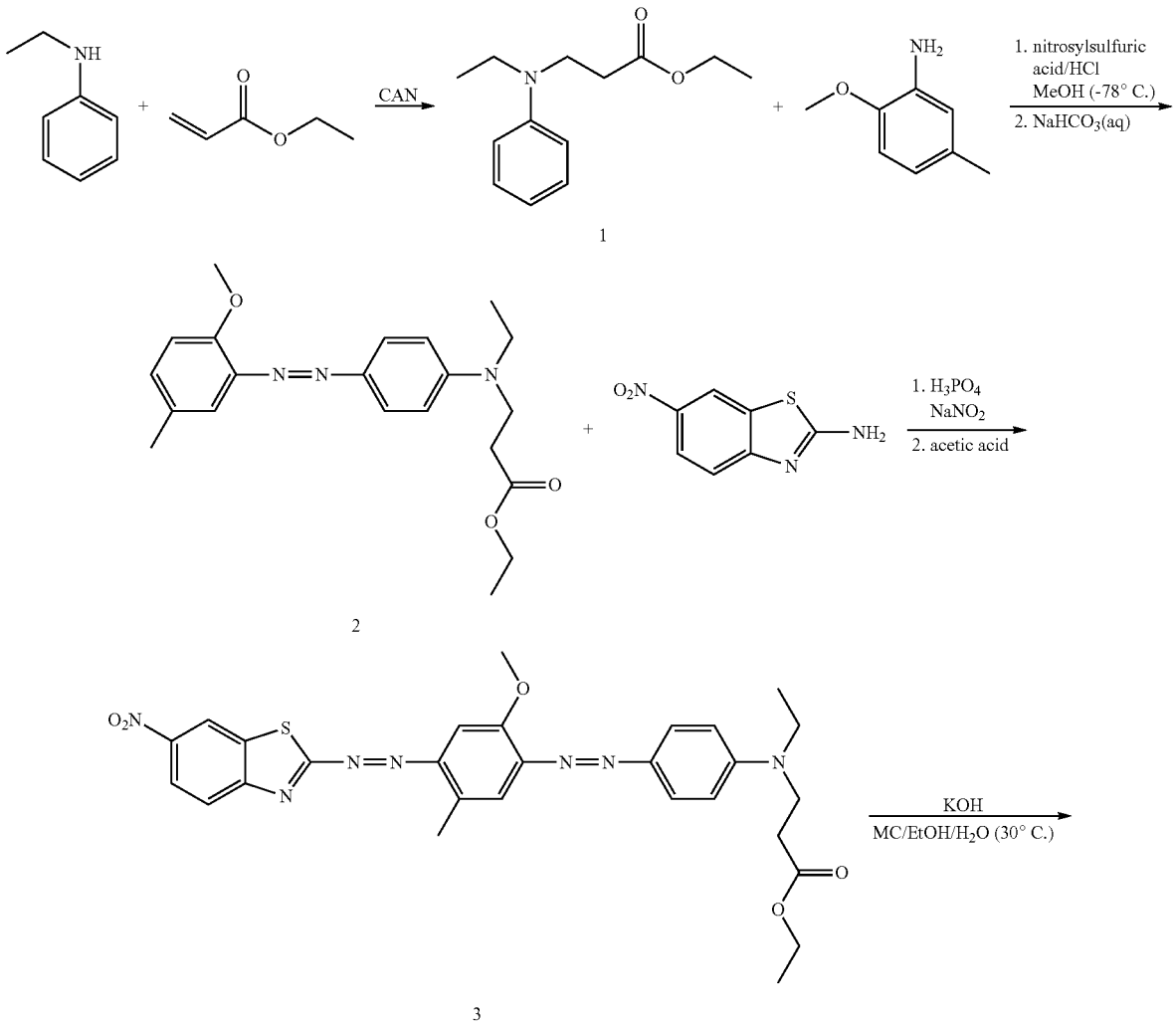

-continued
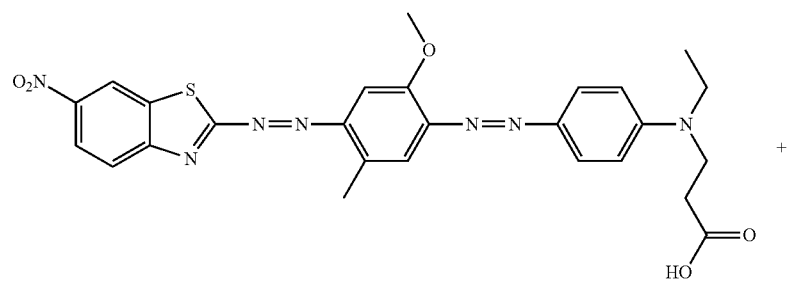
4
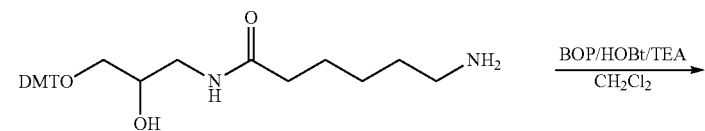
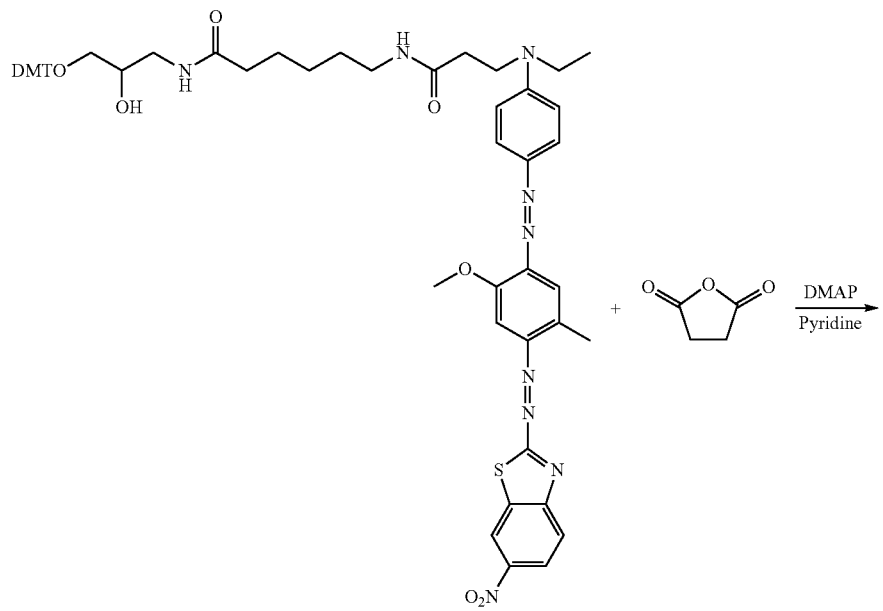
5

-continued
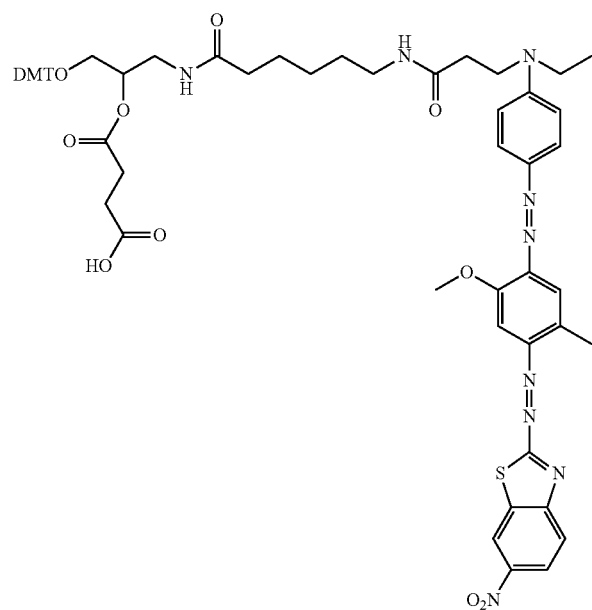
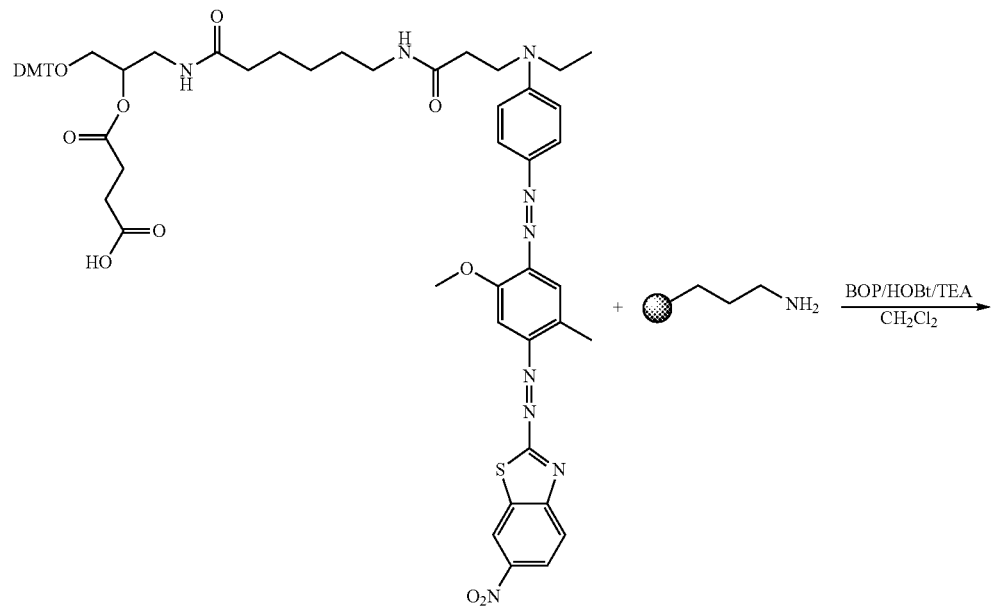

-continued

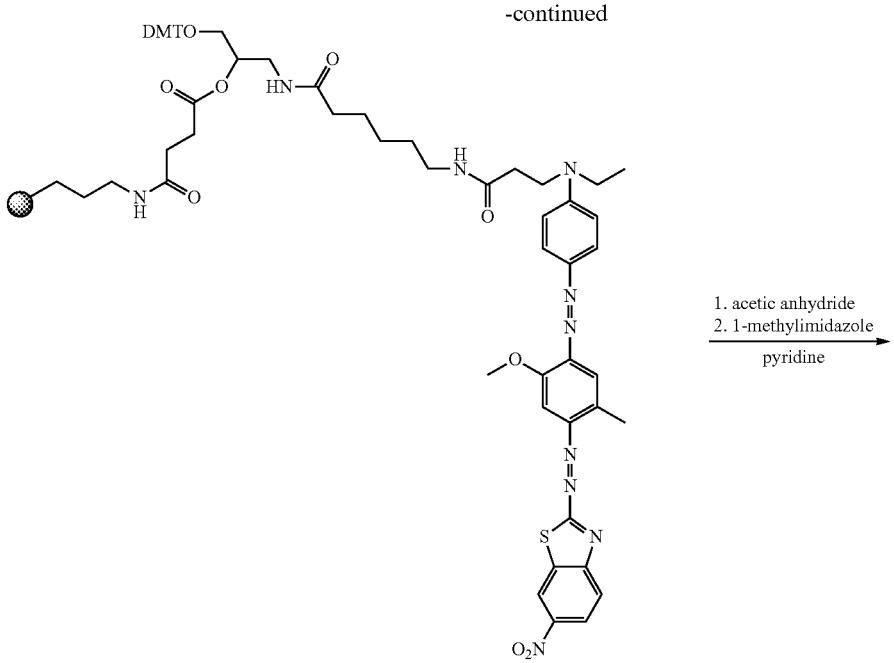

1. acetic anhydride
2. 1-methylimidazole
———————→
pyridine

7

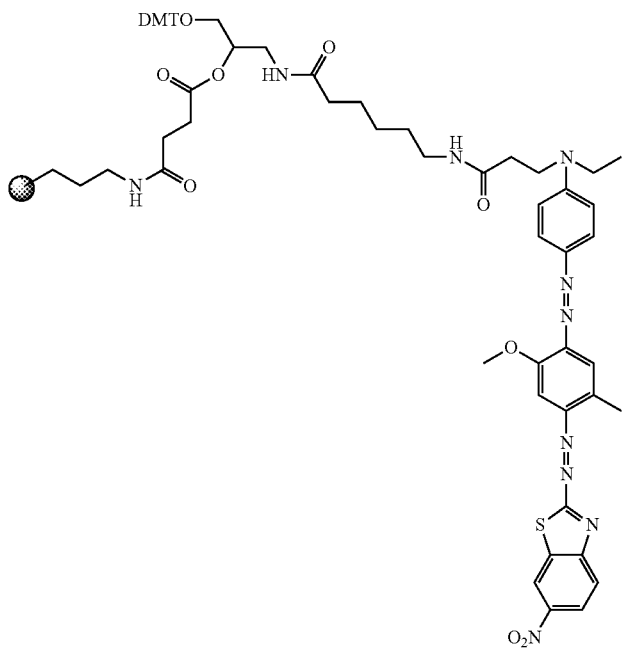

8

3-1: Preparation of Compound of Process 1—Amination 30 g (250 mmol, 1 eq) of N-ethylaniline, 37.2 g (370 mmol, 1.5 eq) of ethyl acrylate, and 13.57 g (25 mmol, 0.1 eq) of cerium (IV) ammonium nitrate were mixed and stirred. The mixture was heated to 60° C. and stirred for 15 hours. The reaction solution was cooled to room temperature and extracted with methylene chloride. The extract was dried with sodium sulfate and filtered. The filtrate was concentrated under reduced pressure and separated by a column. The separated material was concentrated under reduced pressure and dried in a vacuum to afford 47 g of the desired compound (yellow liquid, 85.8%).

$^1$H NMR (300 MHz, CDCl$_3$): 7.27-7.20 ppm (2H, t), 6.73-6.67 ppm (3H, m), 4.20-4.11 ppm (2H, q), 3.67-3.61 ppm (2H, t), 3.43-3.35 ppm (2H, q), 2.63-2.57 ppm (2H, t), 1.31-1.24 ppm (3H, t), 1.19-1.14 ppm (3H, t)

3-2: Preparation of Compound of Process 2—First Azo Coupling 17.37 g (54.67 mmol, 1.5 eq) of nitrosylsulfuric acid, 7.6 g of hydrochloric acid and 400 ml of methanol were mixed and stirred. The mixture was cooled to −78° C. and stirred for 10 minutes. Then, a solution of 5 g (36.45 mmol, 1 eq) of 2-methoxy-5-methylaniline in 50 ml of methanol was added dropwise to the reaction solution, followed by stirring at room temperature for 1 hour. Then, a solution of 8.87 g (40.09 mmol, 1.1 eq) of the process 1 compound in methanol was added dropwise thereto, followed by stirring for 2 hours. Then, the reaction solution was neutralized with a saturated aqueous solution of sodium hydrocarbonate, followed by stirring for 15 hours. The, the solution was concentrated under reduced pressure to remove methanol. The residue was extracted with methylene chloride. The extract was dried with sodium sulfate and filtered. The filtrate was concentrated under reduced pressure and separated by a column. The separated material was concentrated under reduced pressure and dried in a vacuum to afford 6.26 g of the desired compound (orange liquid, 46.5%).

$^1$H NMR (300 MHz, CDCl$_3$): 7.90-7.86 ppm (2H, d), 7.27-7.25 ppm (1H, s), 7.01-6.93 ppm (2H, m), 6.75-6.72 ppm (2H, d), 4.20-4.12 ppm (2H, q), 3.99-3.97 ppm (3H, s), 3.84-3.82 ppm (3H, s), 3.75-3.69 ppm (2H, t), 3.50-3.44 ppm (2H, q), 2.67-2.61 ppm (2H, t), 1.30-1.18 ppm (6H, m)

3-3: Preparation of Compound of Process 3

1.59 g (8.12 mmol, 1 eq) of 2-amino-6-nitro-benzothiazole was added and cooled to 0° C., and 42 ml of phosphoric acid was added thereto. Then, 0.56 g (8.12 mmol, 1 eq) of sodium nitrate was added to the mixture, followed by stirring for 1 hour. Then, a solution of 3 g (8.12 mmol, 1 eq) of the process 2 compound in 15 ml of acetic acid was added dropwise to the reaction solution. After cooling to 0° C., the reaction solution was neutralized with a saturated aqueous solution of sodium hydrocarbonate, and then stirred at room temperature for 15 hours. Then, the solid was filtered, dissolved in 20 ml of methylene chloride, precipitated with 500 ml of ethanol, and filtered. The obtained solid was dried in a vacuum to afford 1.5 g of the desired compound (dark brown solid, 32%).

$^1$H NMR (300 MHz, CDCl$_3$): 8.82-8.81 ppm (1H, d), 8.41-8.37 ppm (1H, d), 8.28-8.24 ppm (1H, d), 7.95-7.91 ppm (2H, d), 7.66-7.60 ppm (2H, d), 6.77-6.74 ppm (2H, d), 4.22-4.14 ppm (2H, q), 4.05-4.04 ppm (3H, s), 3.79-3.73 ppm (2H, t), 3.55-3.50 ppm (2H, q), 2.78-2.77 ppm (3H, s), 2.70-2.64 ppm (2H, t), 1.31-1.21 ppm (6H, m)

3-4: Preparation of Compound of Process 4—Hydrolysis 1.5 g (2.61 mmol, 1 eq) of the process 3 compound, 50 ml of methylene chloride and 50 ml of ethanol were mixed and stirred. A solution of 3.88 g (69.15 mmol, 26.5 eq) of potassium hydroxide in 40 ml of water was added dropwise to the mixture, followed by stirring at 30° C. for 2 days. Then, the reaction solution was concentrated under reduced pressure. The concentrate was neutralized with 1N hydrochloric acid to a pH of 4-5. The formed solid was filtered and washed with water and methanol. Then, the solid was dried in a vacuum to afford 0.9 g of the desired compound (dark brown solid, 63%).

3-5: Preparation of Compound of Process 5—Amidation ($C_9$-spacer)

0.9 g (1.64 mmol, 1 eq) of the process 4 compound, 0.73 g (1.64 mmol, 1 eq) of bis-2-oxo-3-oxazolidinylphosphoric chloride, 0.22 g (1.64 mmol, 1 eq) of 1-hydroxybenzotriazole, 0.83 g (1.64 mmol, 1 eq) of the process 8 compound of Preparation Example 1, and 80 ml of methylene chloride were mixed and stirred. 0.83 g (8.20 mmol, 5 eq) of triethylamine was added to the mixture, followed by stirring for 15 hours. The reaction solution was extracted with methylene chloride. The extract was dried with sodium sulfate and filtered. The filtrate was concentrated under reduced pressure and separated by a column. The separated material was concentrated under reduced pressure and dried in a vacuum to afford 1.55 g of the desired compound (dark blue solid, 91%).

$^1$H NMR (300 MHz, CDCl$_3$): 8.64-8.62 ppm (1H, d), 8.26-8.22 ppm (1H, m), 8.16-8.12 ppm (1H, d), 7.76-7.72 ppm (2H, d), 7.53-7.52 ppm (1H, s), 7.46-7.45 ppm (1H, s), 7.41-7.37 ppm (2H, d), 7.30-7.16 ppm (7H, m), 6.82-6.78 ppm (4H, d), 6.68-6.63 ppm (2H, d), 6.22-6.18 ppm (1H, t), 5.90-5.85 ppm (1H, t), 3.98-3.97 ppm (3H, s), 3.87-3.86 ppm (1H, s), 3.76-3.75 ppm (6H, s), 3.57-3.48 ppm (4H, m), 3.37-3.36 ppm (1H, s), 3.28-3.07 ppm (6H, m), 2.66-2.65 ppm (3H, s), 2.64-2.60 ppm (1H, d), 2.51-2.46 ppm (2H, t), 2.11-2.05 ppm (2H, t), 1.60-1.43 ppm (4H, m), 1.34-1.16 ppm (4H, m)

3-6: Preparation of Compound of Process 6—Succinylation 1.55 g (1.50 mmol, 1 eq) of the process 5 compound, 0.45 g (4.49 mmol, 3 eq) of succinic anhydride, 0.02 g (0.15 mmol, 0.1 eq) of N,N-dimethylaminopyridine and 30 ml of pyridine were mixed, and stirred at 50° C. for 20 hours. The mixture was cooled to room temperature and concentrated under reduced pressure. The concentrate was extracted with methylene chloride. The extract was dried with sodium sulfate and filtered. The filtrate was concentrated under reduced pressure and separated by a column (methylene chloride: methanol=20:1). The separated material was concentrated under reduced pressure and dried in a vacuum to afford 1.38 g of the desired compound (dark purple solid, 81%).

$^1$H NMR (300 MHz, CDCl$_3$): 8.79-8.78 ppm (1H, d), 8.40-8.35 ppm (1H, dd), 8.27-8.23 ppm (1H, d), 7.91-7.87 ppm (2H, d), 7.65-7.57 ppm (2H, m), 7.43-7.39 ppm (2H, d), 7.31-7.19 ppm (7H, m), 6.84-6.80 ppm (4H, d), 6.75-6.71 ppm (2H, d), 6.38-6.37 ppm (1H, m), 6.01-6.00 ppm (1H, t), 5.21-5.20 ppm (1H, s), 4.04-4.03 ppm (3H, s), 3.91-3.70 ppm (8H, m), 3.50-3.18 ppm (9H, m), 2.79-2.65 ppm (8H, m), 2.54-2.51 ppm (2H, t), 2.15-2.12 ppm (2H, t), 1.66-1.49 ppm (4, m), 1.35-1.19 ppm (4H, m)

3-7: Preparation of Compound of Process 7—LCAA-CPG Coupling 2 g of LCAA-CPG, 0.18 g (0.16 mmol, 2 eq) of the process compound, 0.07 g (0.16 mmol, 2 eq) of bis-2-oxo-3-oxazolidinylphosphoric chloride, 0.02 g (0.16 mmol, 2 eq) of 1-hydroxybenzotriazole, 30 ml of methylene chloride and 0.09 g (0.88 mmol, 11 eq) of triethylamine were mixed, and stirred for 20 hours. After completion of the reaction, the reaction was filtered, washed with methanol, and dried in a vacuum to afford 2 g of the desired compound.

3-8: Preparation of Compound of Process 8—Capping 2.9 g of the process 7 compound, 40 ml of pyridine, 5 ml of acetic anhydride and 3.2 ml of 1-methylimidazole were mixed, and stirred for 1 hour. The reaction solution was filtered and washed with methanol. The filtrate was dried in a vacuum to afford 23.5 g of the desired compound (purple solid).

PREPARATION EXAMPLE 4
Preparation of Compound of Formula 14 (Quencher 545)
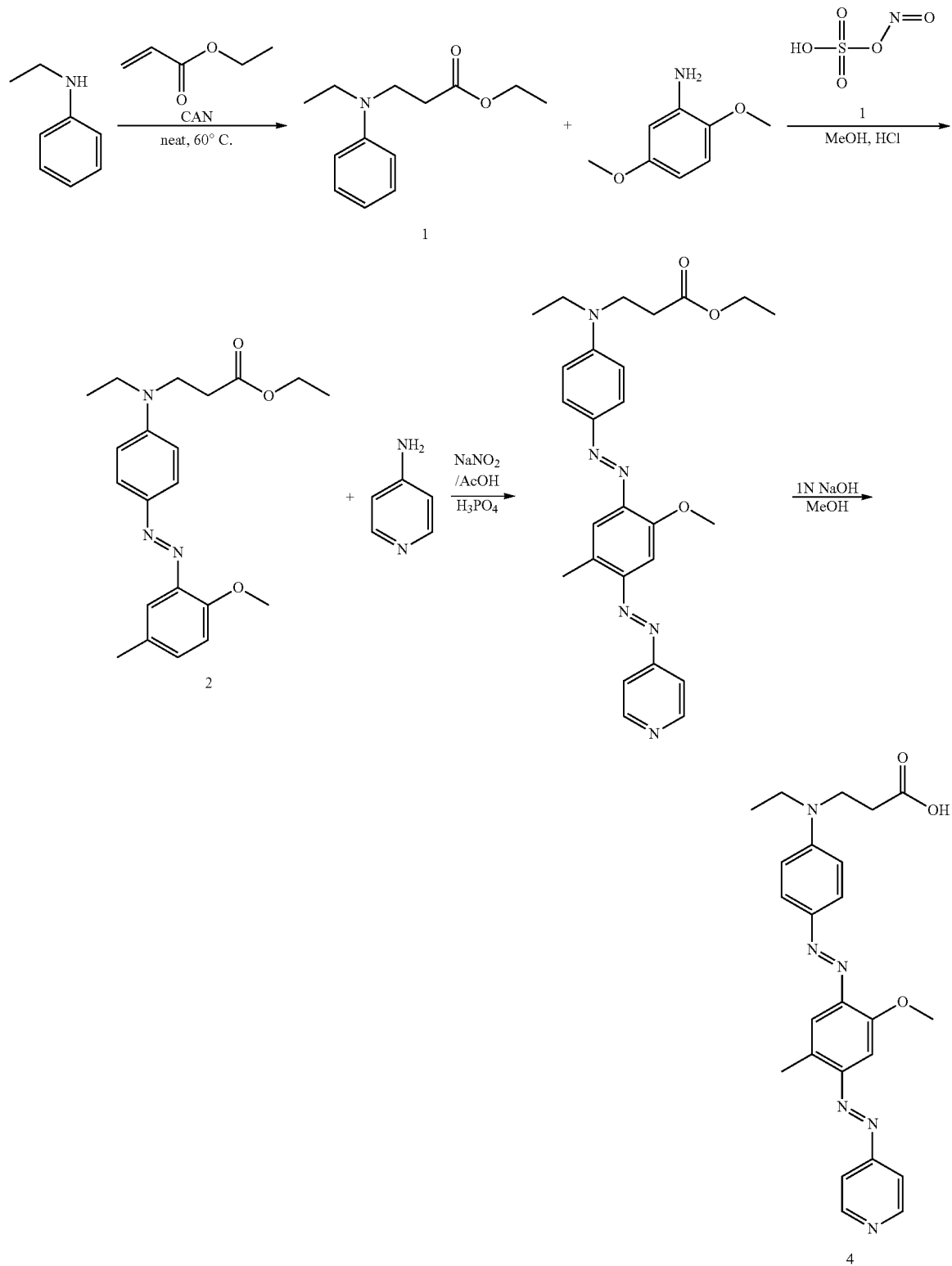

-continued
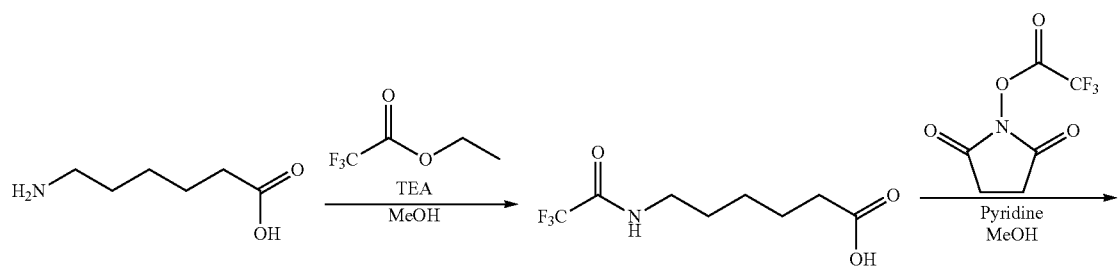
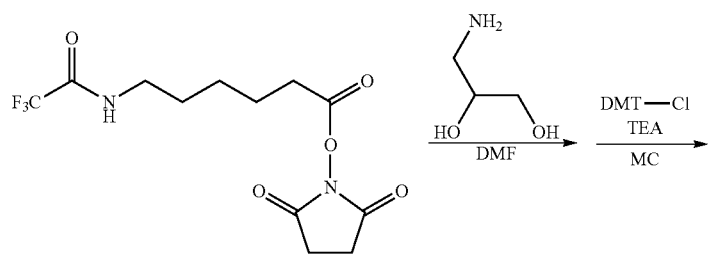
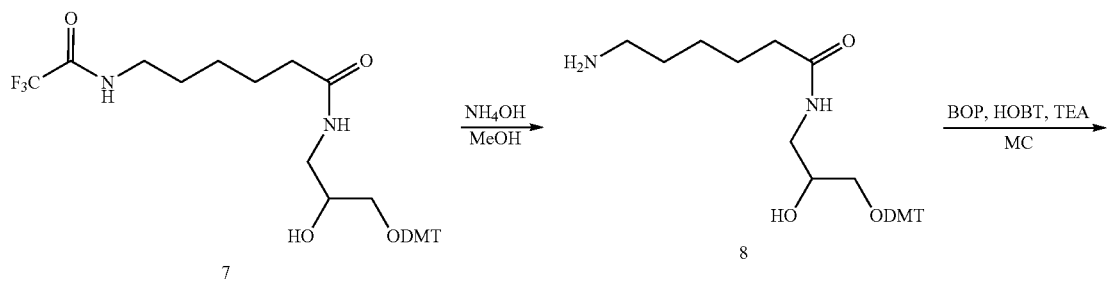
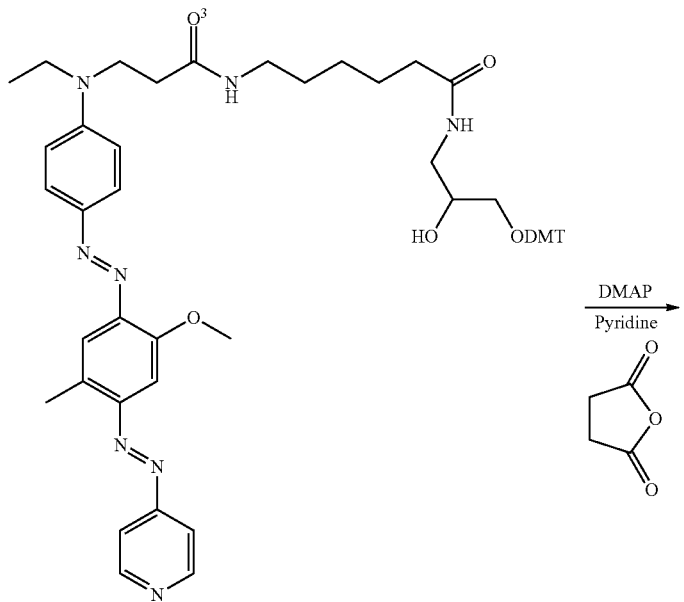

-continued
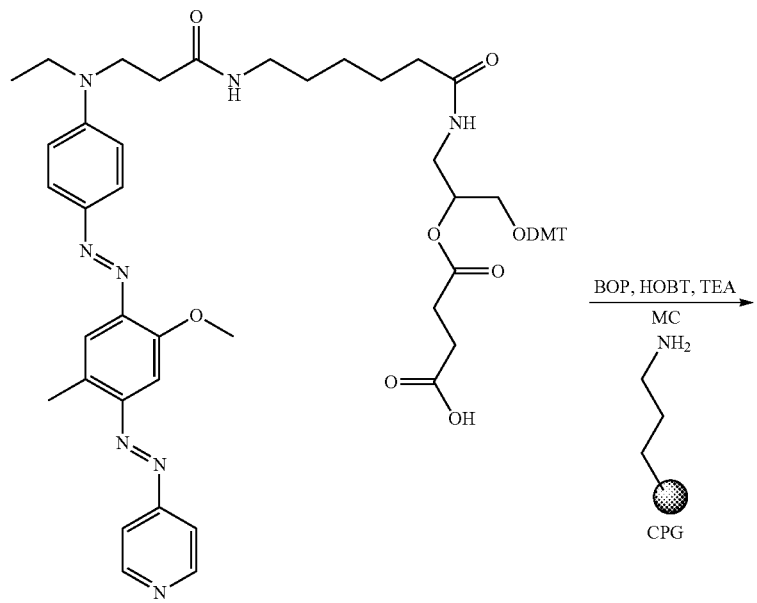
10
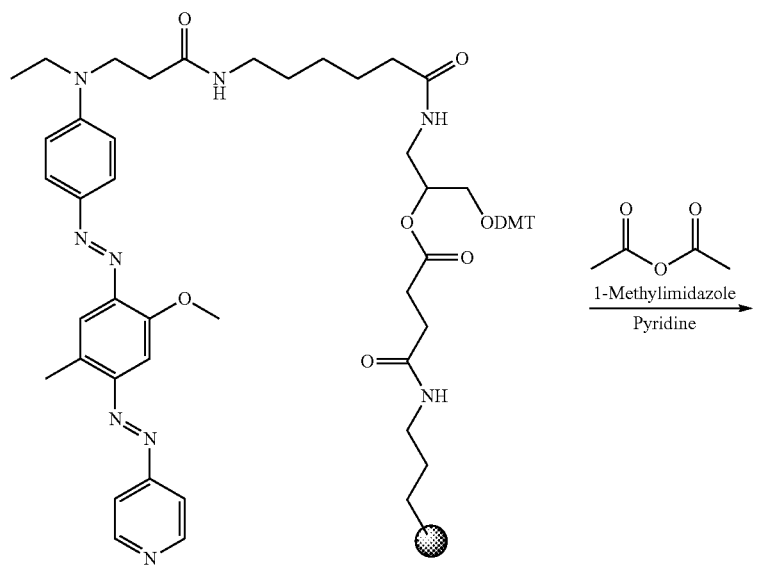
11

-continued

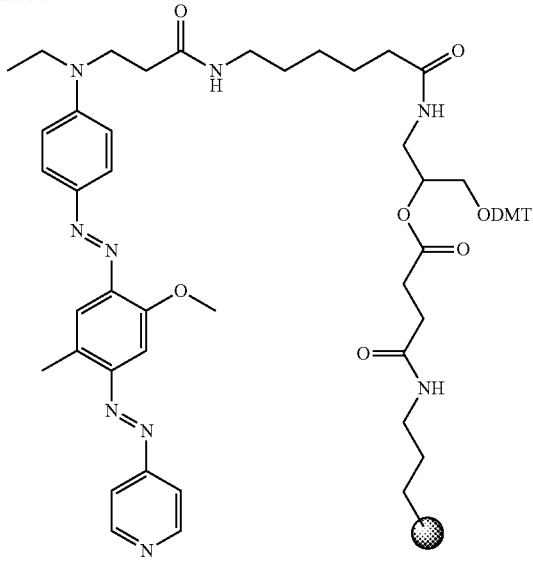

CPG

12

4-1: Preparation of Compound of Process 1—Amination 10 g (83 mmol, 1 eq) of N-ethylaniline, 12.5 g (120 mmol, 1.5 eq) of ethyl acrylate, and 4.5 g (8.3 mmol, 0.1 eq) of cerium ammonium nitrate were mixed and stirred. The mixture was heated to 60° C. and stirred for 1 day. Then, the reaction solution was cooled to room temperature and extracted with methylene chloride. The extract was dried with sodium sulfate and filtered. The filtrate was concentrated under reduced pressure and separated by a column. The separated material was concentrated under reduced pressure and dried in a vacuum to afford 12.53 g (68.2%) of the desired compound.

$^1$H NMR (300 MHz, CDCl$_3$):7.25-7.17(2H, t), 6.71-6.64 (3H, m), 4.18-4.09(2H, q), 3.65-3.58(2H, t), 3.41-3.32(2H, q), 2.61-2.54(2H, t), 1.28-1.21(3H, t), 1.17-1.08(3H, t)

4-2: Preparation of Compound of Process 2—First Azo Coupling 17.37 g (54.67 mmol, 1.5 eq) of nitrosylsulfuric acid, 20 ml of hydrochloric acid and 20 ml of methanol were mixed and stirred. The mixture was cooled to -78r and stirred for 20 minutes. A solution of 5 g (36.45 mmol, 1 eq) of 2,5-methoxyaniline in 120 ml of methanol was added dropwise to the reaction solution, followed by stirring at room temperature for 1 hour. Then, a solution of 8.87 g (40.09 mmol, 1.1 eq) of the process 1 compound in methanol was added dropwise to the reaction solution, followed by stirring for 1 hour. Then, the reaction solution was neutralized with a saturated aqueous solution of sodium hydrocarbonate to a pH of 6-8. After completion of neutralization, the solution was stirred for 1 day. Then, the reaction solution was concentrated under reduced pressure to remove methanol. The concentrate was extracted with methylene chloride and filtered. The filtrate was concentrated under reduced pressure and separated by a column. The separated material was concentrated under reduced pressure and dried in a vacuum to afford 6.26 g (46.5%) of the desired compound.

$^1$H NMR (300 MHz, CDCl$_3$):7.88-7.85 (2H, d), 7.44-7.42 (1H, s), 7.17-7.14 (1H, d), 6.96-6.93 (1H, d), 6.75-6.71 (2H, d), 4.20-4.08 (2H, m), 4.00-3.95 (3H, s), 3.74-3.69 (2H, m), 3.51-3.44 (2H, q), 2.67-2.62 (2H, t), 2.34-2.32 (3H, s), 1.32-1.19 (6H, m)

4-3: Preparation of Compound of Process 3—Second Azo Coupling 0.79 g (11.40 mmol, 1 eq) of sodium nitrate and 10 ml of phosphoric acid were mixed and stirred. The mixture was cooled to 0° C. and stirred for 20 minutes. Then, 1.07 g (11.40 mmol, 1 eq) of 4-aminopyridine was added thereto, followed by stirring at room temperature for 30 minutes. Then, a solution of 4.21 g (11.40 mmol, 1 eq) of the process 2 compound in 60 ml of acetic acid was added dropwise to the reaction solution, followed by stirring for 1 hour. Then, the reaction solution was added to 100 ml of distilled water and neutralized with a saturated aqueous solution of sodium hydrocarbonate to a pH of 4-8, followed by stirring for 1 day. Next, the reaction solution was extracted with methylene chloride. The extract was dried with sodium sulfate and filtered. The filtrate was concentrated under reduced pressure and separated by a column. The separated material was concentrated under reduced pressure and dried in a vacuum to afford 0.25 g (4.6%) of the desired compound.

$^1$H NMR (300 MHz, CDCl$_3$): 8.82-8.80 (2H, d), 7.93-7.90 (2H, d), 7.74-7.72 (2H, d), 7.60-7.58 (1H, s), 7.45-7.43 (1H, s), 6.76-6.73 (2H, d), 4.20-4.13 (2H, q), 4.05-4.01 (3H, s), 3.77-3.72 (2H, t), 3.52-3.47 (2H, q), 2.75-2.73 (3H, s), 2.68-2.63 (2H, t), 1.30-1.21 (6H, m)

4-4: Preparation of Compound of Process 4—Hydrolysis 0.25 g (0.53 mmol, 1 eq) of the process 3 compound, 20 ml of methanol and 20 ml of methylene chloride were mixed and stirred. 1.58 ml (1.58 mmol, 3 eq) of 1N sodium hydroxide was added to the mixture and stirred for 3 days. Then, 1.58 ml (1.58 mmol, 1 eq) of 1N sodium hydroxide was added to the solution, which was then stirred for 1 day and concentrated under reduced pressure. Next, the reaction solution was added to 100 ml of distilled water and stirred. The reaction solution was neutralized with 1N hydrochloric acid to a pH of 4-7, and extracted with methylene chloride. The extract was dried with sodium sulfate and filtered. The filtrate was concentrated under reduced pressure and dried in a vacuum to afford 0.24 g of the desired compound.

¹H NMR (300 MHz, CDCl₃):8.79-8.77 (2H, d), 7.92-7.89 (2H, d), 7.74-7.71 (2H, d), 7.59-7.57 (1H, s), 7.43-7.41 (1H, s), 6.78-6.75 (2H, d), 4.05-4.03 (3H, s), 3.77-3.75 (2H, t), 3.54-3.51 (2H, q), 2.75-2.72 (5H, m), 1.27-1.22 (3H, t)

4-5: Preparation of Compound of Process 5—Amine Protection 15 g (114 mmol, 1 eq) of 6-aminocapric acid, 48 ml (342 mmol, 3 eq) of triethylamine and 230 ml of methanol were mixed and stirred. 15 ml (125 mmol, 1.1 eq) of ethyl trifluoroacetate was added to the mixture, followed by stirring for 1 day. Then, the reaction solution was concentrated under reduced pressure and extracted with ethyl acetate. The organic layer was dried with magnesium sulfate and filtered. The filtrate was concentrated under reduced pressure and dried in a vacuum to afford 16.67 g (64%) of the desired compound.

¹H NMR (300 MHz, DMSO-d₆):11.99-11.97 (1H, s), 9.39-9.37 (1H, s), 3.20-3.12 (2H, q), 2.22-2.16 (2H, t), 1.55-1.41 (4H, m), 1.31-1.19 (2H, m)

4-6: Preparation of Compound of Process 6—NHS Esterification 5.28 g (23.24 mmol, 1 eq) of the process 5 compound, 120 ml of methanol and 9.38 ml (116.2 mmol, 5 eq) of pyridine were mixed and stirred. 8.81 g (41.83 mmol, 1.8 eq) of N-succinimidyl trifluoroacetate was added to the mixture, followed by stirring for 1 day. The reaction solution was concentrated under reduced pressure and extracted with methylene chloride. The organic layer was dried with dried with magnesium sulfate and filtered. The filtrate was concentrated under reduced pressure. The concentrate was dried in a vacuum to afford 7.08 g of the desired compound (white solid, 94.8%).

¹H NMR (300 MHz, CDCl₃): 6.80-6.78 ppm (1H, s), 3.40-3.32 ppm (2H, q), 2.84-2.82 ppm (4H, s), 2.64-2.58 ppm (2H, t), 1.83-1.73 ppm (2H, m), 1.67-1.57 ppm (2H, m), 1.52-1.44 ppm (2H, m)

4-7: Preparation of Compound of Process 7—Amidation (C₆-spacer) and DMT Addition 1.17 g (3.61 mmol, 1 eq) of the process 6 compound, 6 ml of dimethylformamide and 0.49 g (5.42 mmol, 1.5 eq) of 3-amino-1,2-propanediol were mixed and stirred for 1 day. 50 ml of methylene chloride was added to the mixture, followed by cooling to 0° C. Then, 1.83 g (5.42 mmol, 1 eq) of dimethyl chloride was added to the reaction solution, followed by stirring. Then, a solution of 3.03 ml (21.68 mmol, 4 eq) of triethylamine in 10 ml of methylene chloride was added dropwise to the reaction solution. Next, the reaction solution was stirred at room temperature for 4 hours and concentrated under reduced pressure. The concentrate was extracted with methylene chloride. The extract was magnesium sulfate and filtered. The filtrate was concentrated under reduced pressure and separated by a column. The separated material was concentrated under reduced pressure and dried in a vacuum to afford 0.92 g (41.9%) of the desired compound.

¹H NMR (300 MHz, CDCl₃): 7.55-7.53 (1H, s), 7.43-7.39 (2H, m), 7.32-7.15 (7H, m), 6.83-6.78 (4H, d), 6.17-6.15 (1H, s), 3.87-3.85 (1H, m), 3.75-3.73 (6H, s), 3.68-3.65 (1H, m), 3.53-3.46 (1H, m), 3.32-3.22 (2H, m), 3.20-3.09 (2H, m), 2.11-2.04 (2H, t), 1.61-1.46 (4H, m), 1.33-1.24 (2H, m)

4-8: Preparation of Compound of Process 8—Amine Deprotection 0.84 g (1.39 mmol, 1 eq) of the process 7 compound and 5 ml of methanol were mixed and stirred. 4.26 ml (27.8 mmol, 20 eq) of ammonia solution (25%) was added dropwise to the mixture, followed by stirring for 1 day. The reaction solution was extracted with methylene chloride. The extract was dried with sodium sulfate and filtered. The filtrate was concentrated under reduced pressure and dried in a vacuum to afford 0.78 g (>100%) of the desired compound.

¹H NMR (300 MHz, CDCl₃):7.42-7.38 (2H, m), 7.31-7.17 (7H, m), 6.83-6.78 (4H, d), 6.61-6.59 (1H, s), 3.91-3.89 (1H, m), 3.76-3.74 (6H, s), 3.54-3.48 (2H, m), 3.20-3.09 (2H, m), 2.93-2.89 (2H, m), 2.16-2.10 (2H, m), 1.70-1.56 (4H, m), 1.38-1.31 (2H, m)

4-9: Preparation of Compound of Process 9—Amidation (C₉-spacer)

0.24 g (0.54 mmol, 1 eq) of the process 4 compound, 0.26 g (0.59 mmol, 1.1 eq) of bis-2-oxo-3-oxazolidinylphosphoric chloride, 0.08 g (0.59 mmol, 1.1 eq) of 1-hydroxybenzotriazole, 0.3 g (0.59 mmol, 1.1 eq) of the process 8 compound, and 100 ml of methylene chloride were mixed and stirred. 0.37 ml (2.69 mmol, 5 eq) of triethylamine was added to the mixture, followed by stirring for 15 hours. Then, the reaction solution was concentrated under reduced pressure and extracted with ethyl acetate. The organic layer was dried with sodium sulfate and filtered. The filtrate was concentrated under reduced pressure and separated by a column. The separated material was concentrated under reduced pressure and dried in a vacuum to afford 0.46 g (91.1%) of the desired compound.

¹H NMR (300 MHz, CDCl₃): 8.82-8.79 (2H, d), 7.91-7.88 (2H, d), 7.74-7.72 (2H, d), 7.59-7.57 (1H, s), 7.43-7.34 (3H, m), 7.30-7.18 (7H, m), 6.82-6.79 (4H, d), 6.75-6.72 (2H, d), 5.94-5.92 (1H, t), 5.83-5.82 (1H, t), 4.03-4.01 (3H, s), 3.86-3.80 (1H, m), 3.77-3.74 (6H, s), 3.57-3.44 (4H, m), 3.27-3.08 (6H, m), 2.76-2.74 (3H, s), 2.51-2.40 (2H, t), 2.10-2.05 (2H, t), 1.61-1.42 (4H, m), 1.31-1.17 (5H, m)

4-10: Preparation of Compound of Process 10—Succinylation 0.46 g (0.49 mmol, 1 eq) of the process 9 compound, 0.25 g (2.46 mmol, 5 eq) of succinic anhydride, 0.03 g (0.25 mmol, 0.5 eq) of N,N-dimethylaminopyridine, and 35 ml of pyridine were mixed and stirred. The mixture was heated to 60° C. and stirred for 1 day. Then, the reaction solution was cooled to room temperature, and concentrated under reduced pressure. The concentrate was extracted with methylene chloride. The extract was dried with sodium sulfate and filtered. The filtrate was concentrated under reduced pressure and separated by a column. The separated material was concentrated under reduced pressure and dried in a vacuum to afford 0.03 g (5.9%) of the desired compound.

¹H NMR (300 MHz, CDCl₃): 8.83-8.81 (2H, d), 7.92-7.89 (2H, d), 7.74-7.73 (2H, d), 7.60-7.58 (1H, s), 7.43-7.33 (3H, m), 7.31-7.17 (7H, m), 6.83-6.80 (4H, d), 6.74-6.71 (2H, d), 6.45-6.35 (1H, s), 5.31-5.17 (1H, s), 4.05-4.03 (3H, s), 3.79-3.77 (1H, m), 3.76-3.74 (6H, s), 3.48-3.46 (4H, m), 3.26-3.18 (6H, m), 2.90-2.60 (7H, m), 2.64-2.62 (2H, m), 2.53-2.43 (2H, m), 1.60-1.28 (4H, m), 1.25-1.18 (5H, m)

4-11: Preparation of Compound of Process 11—LCAA-CPG Coupling 16.8 g of LCAA-CPG, 1.14 g (1.1 mmol, 1 eq) of the process 10 compound, 0.5 g (1.1 mmol, 1 eq) of bis-2-oxo-3-oxazolidinylphosphoric chloride, 0.15 g (1.1 mmol, 1 eq) of 1-hydroxybenzotriazole, 100 ml of methylene chloride and 0.6 ml (5.5 mmol, 5 eq) of triethylamine were mixed and stirred at room temperature for 1 day. The reaction solution was filtered and washed with methanol. The filtrate was dried in a vacuum to yield 17.16 g of the desired compound (purple solid).

4-12: Preparation of Compound of Process 12—Capping 17.16 g of the process 11 compound, 90 ml of pyridine, 3.59 ml (38 mmol) of acetic anhydride, and 18 ml (225 mmol) of 1-methyl imidazole were mixed and stirred for 1.5 hours. The reaction solution was filtered and washed with methanol. The reaction solution was dried in a vacuum to afford 16.7 g of the desired compound.

PREPARATION EXAMPLE 5
Preparation of Compound of Formula 17 (Quencher 530)
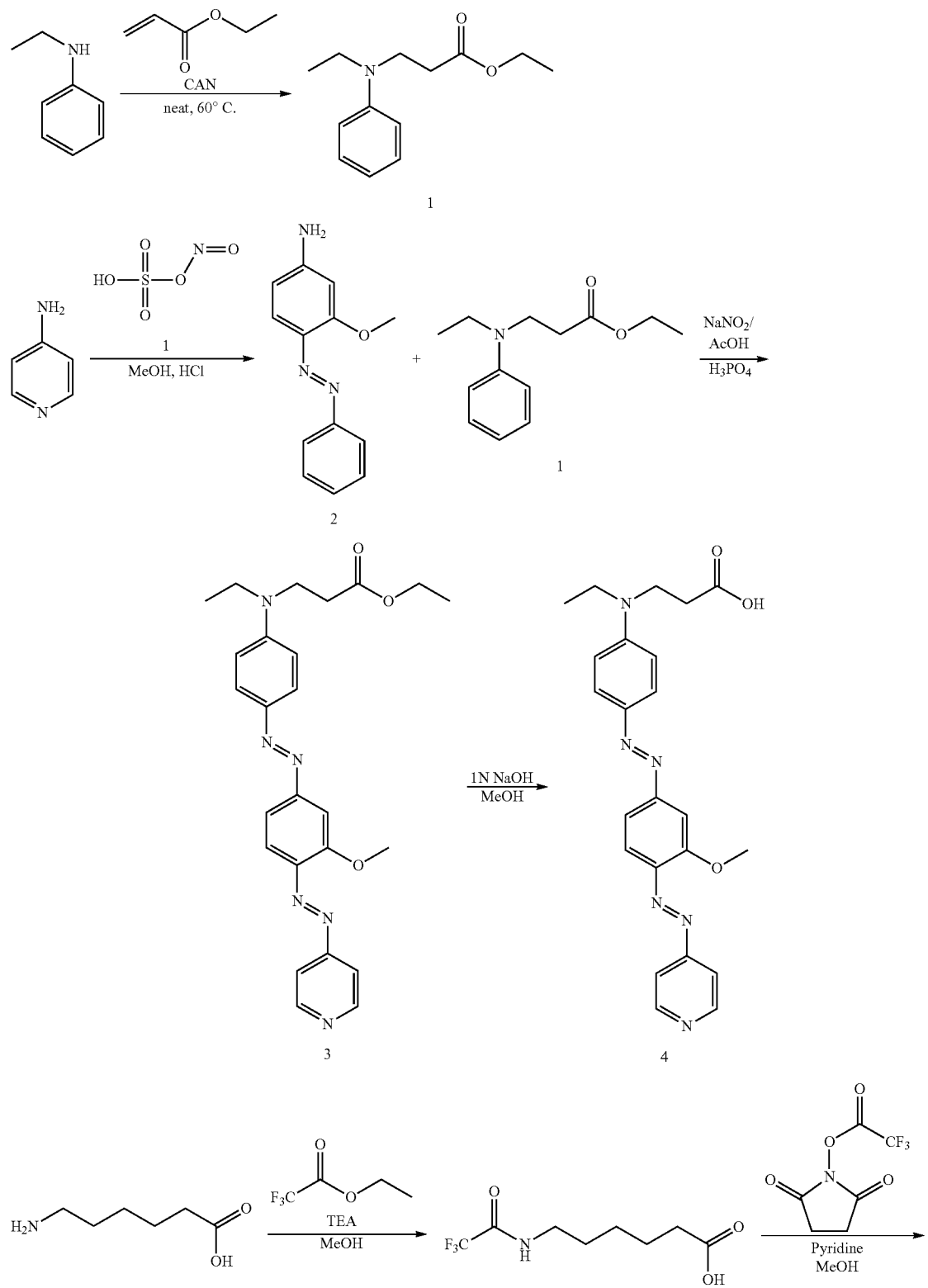

-continued
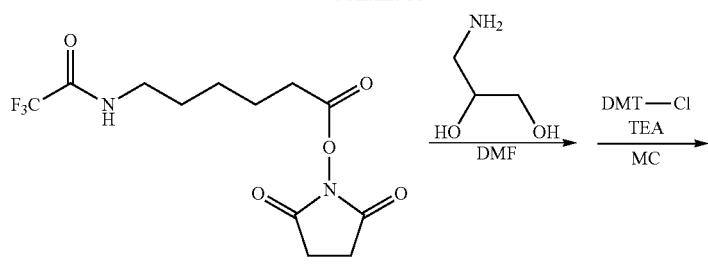
6
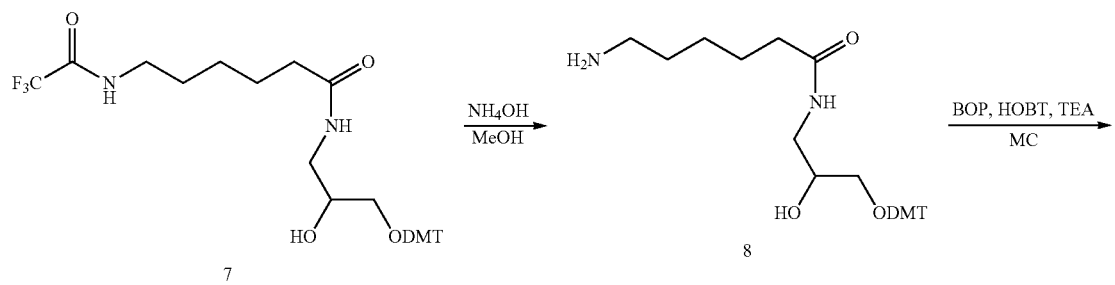
7    8
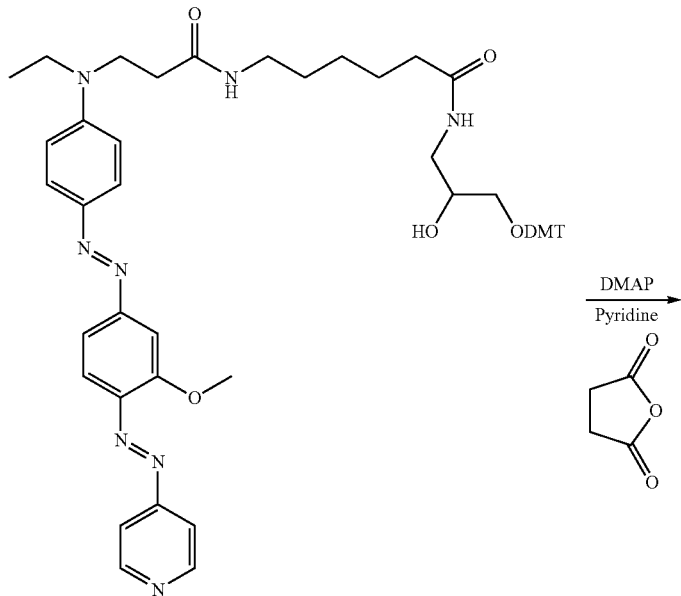
9

-continued
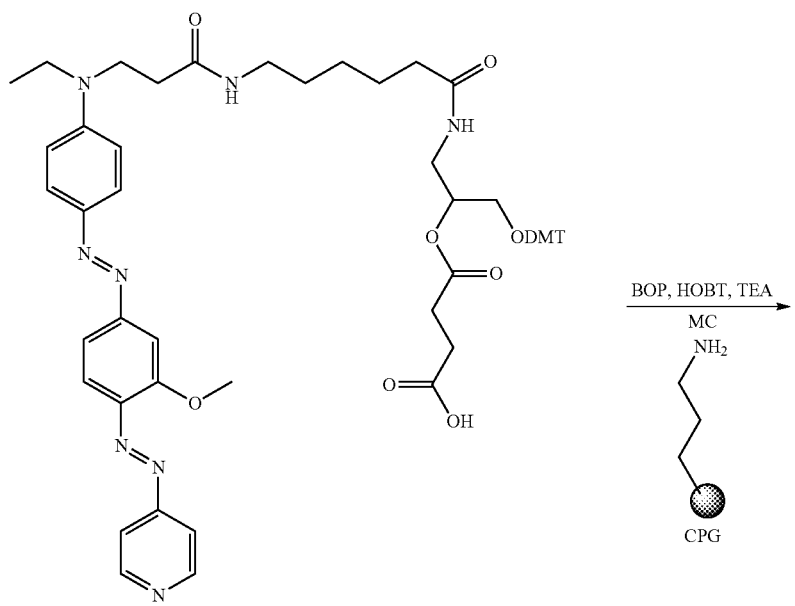
10
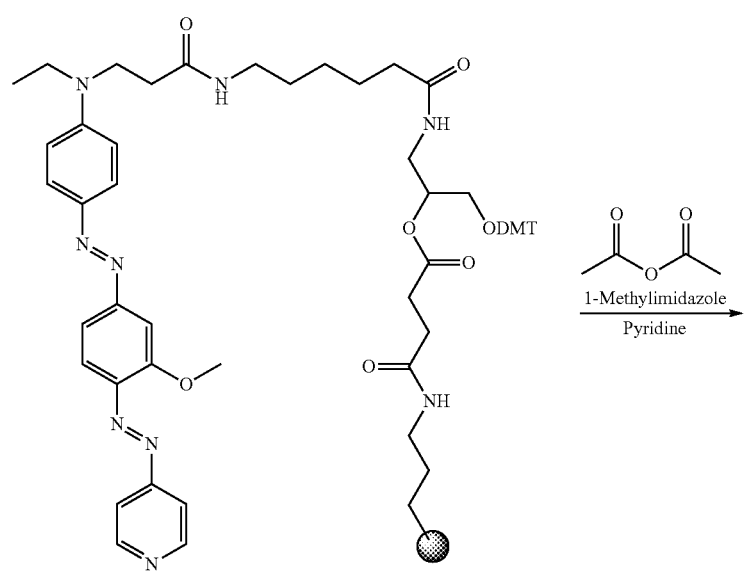
11

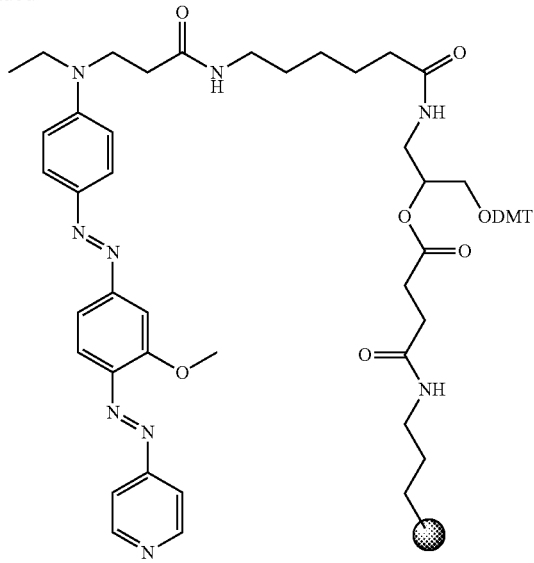

CPG
12

5-1: Preparation of Compound of Process 1—Amination 10 g (83 mmol, 1 eq) of N-ethylaniline, 12.5 g (120 mmol, 1.5 eq) of ethyl acrylate, and 4.5 g (8.3 mmol, 0.1 eq) of cerium (IV) ammonium nitrate were mixed and stirred. The mixture was heated to 60° C. and stirred for 1 day. Then, the reaction solution was cooled to room temperature and extracted with methylene chloride. The extract was dried with sodium sulfate and filtered. The filtrate was concentrated under reduced pressure and separated. The separated material was concentrated under reduced pressure and dried in a vacuum to afford 12.53 g (68.2%) of the desired compound.

$^1$H NMR (300 MHz, CDCl$_3$):7.25-7.17(2H, t), 6.71-6.64 (3H, m), 4.18-4.09(2H, q), 3.65-3.58(2H, t), 3.41-3.32(2H, q), 2.61-2.54(2H, t), 1.28-1.21(3H, t), 1.17-1.08(3H, t)

5-2: Preparation of Compound of Process 2—First Azo Coupling 3.67 g (53.12 mmol, 1.5 eq) of nitrosylsulfuric acid added, cooled to 0° C. and stirred for 5 minutes. Then, 100 ml of phosphoric acid was added to the reaction solution, followed by stirring for 20 minutes. Then, 5 g (53.12 mmol) of 4-aminopyridine was added to the reaction solution, followed by stirring for 40 minutes. Then, the reaction solution was neutralized and stirred at room temperature for 1 day. Next, the solution was extracted with methylene chloride. The filtrate was concentrated under reduced pressure and separated by a column. The separated material was concentrated under reduced pressure and dried in a vacuum to afford 2.07 g (25.6%) of the desired compound.

$^1$H NMR (300 MHz, CDCl$_3$):8.70-8.68 (2H, d), 7.76-7.73 (1H, d), 7.63-7.61 (2H, d), 6.29-6.26 (2H, m), 4.41-4.13 (2H, br), 3.97-3.95 (3H, s)

5-3: Preparation of Compound of Process 3—Second Azo Coupling 0.63 g (9.07 mmol, 1.5 eq) of sodium nitrate and 20 ml of phosphoric acid were added and stirred. The mixture was cooled to 0° C. and stirred for 20 minutes. A solution of 2.07 g (9.07 mmol, 1.5 eq) of the process 2 compound in 30 ml of acetic acid was added dropwise to the reaction solution, followed by stirring for 40 minutes. Then, a solution of 1.34 g (6.05 mmol, 1 eq) of the process 1 compound in 20 ml of acetone was added to the reaction solution, followed by stirring for 40 minutes. Then, the reaction solution was neutralized with a saturated aqueous solution of sodium hydrocarbonate, followed by stirring for 1 day. The reaction solution was extracted with methylene chloride. The extract was dried with sodium sulfate and filtered. The filtrate was concentrated under reduced pressure and separated by a column. The separated material was concentrated under reduced pressure and dried in a vacuum to afford 0.11 g (3.9%) of the desired compound.

$^1$H NMR (300 MHz, CDCl$_3$):8.80-8.78 (2H, d), 7.93-7.90 (2H, d), 7.86-7.83 (1H, d), 7.72-7.70 (2H, d), 7.60-7.58 (1H, s), 7.55-7.52 (1H, d), 6.78-6.75 (2H, d), 4.21-4.14 (5H, m), 3.78-3.73 (2H, t), 3.56-3.49 (2H, q), 2.69-2.65 (2H, t), 1.30-1.22 (6H, m)

5-4: Preparation of Compound of Process 4—Hydrolysis 0.07 g (0.15 mmol, 1 eq) of the process 3 compound, 10 ml of methanol and 10 ml of methylene chloride were mixed and stirred. 0.46 ml (0.46 mmol, 3 eq) of 1N sodium hydroxide was added to the mixture, followed by stirring for 1 day. Next, 1.58 ml (1.58 mmol, 1 eq) of 1N sodium hydroxide was added to the reaction solution, followed by stirring for 1 day. Then, the reaction solution was concentrated under reduced pressure. Then, 50 ml of distilled water was added to the reaction solution, followed by stirring. The reaction solution was neutralized with 1N hydrochloric acid to a pH of 4, and extracted with methylene chloride. The extract was dried with sodium sulfate and filtered. The filtrate was concentrated under reduced pressure and dried in a vacuum to afford 0.06 g (92.8%) of the desired compound.

$^1$H NMR (300 MHz, CDCl$_3$):8.77-8.75 (2H, d), 7.90-7.87 (2H, d), 7.83-7.80 (1H, d), 7.73-7.71 (2H, d), 7.59-7.57 (1H, s), 7.53-7.50 (1H, d), 6.80-6.77 (2H, d), 4.14-4.12 (3H, s), 3.79-3.77 (2H, t), 3.56-3.53 (2H, q), 2.75-2.71 (2H, t), 1.30-1.22 (3H, m)

5-5: Preparation of Compound of Process 5—Amine Protection 15 g (114 mmol, 1 eq) of 6-aminocapric acid, 48 ml (342 mmol, 3 eq) of triethylamine and 230 ml of methanol were added and stirred. 15 ml (125 mmol, 1.1 eq) of ethyl trifluoroacetate was added to the mixture, followed by stirring for 1 day. Then, the reaction solution was concentrated under reduced pressure and extracted with ethyl acetate. The organic layer was dried with magnesium sulfate and filtered. The filtrate was concentrated under reduced pressure and dried in a vacuum to afford 16.67 g (64%) of the desired compound.

$^1$H NMR (300 MHz, DMSO-$d_6$):11.99-11.97 (1H, s), 9.39-9.37 (1H, s), 3.20-3.12 (2H, q), 2.22-2.16 (2H, t), 1.55-1.41 (4H, m), 1.31-1.19 (2H, m)

5-6: Preparation of Compound of Process 6—NHS Esterification 5.28 g (23.24 mmol, 1 eq) of the process 5 compound, 120 ml of methanol and 9.38 ml (116.2 mmol, 5 eq) of pyridine were mixed and stirred. 8.81 g (41.83 mmol, 1.8 eq) of N-succinimidyl trifluoroacetate was added to the reaction solution, followed by stirring for 1 day. Then, the reaction solution was concentrated under reduced pressure and extracted with methylene chloride. The organic layer was dried with magnesium sulfate and filtered. The filtrate was concentrated under reduced pressure and dried in a vacuum to afford 7.08 g of the desired compound (white solid, 94.8%).

$^1$H NMR (300 MHz, CDCl$_3$): 6.80-6.78 ppm (1H, s), 3.40-3.32 ppm (2H, q), 2.84-2.82 ppm (4H, s), 2.64-2.58 ppm (2H, t), 1.83-1.73 ppm (2H, m), 1.67-1.57 ppm (2H, m), 1.52-1.44 ppm (2H, m)

5-7: Preparation of Compound of Process 7—Amidation ($C_6$-spacer) and DMT Addition 1.17 g (3.61 mmol, 1 eq) of the process 6 compound, 6 ml of dimethylformamide, and 0.49 g (5.42 mmol, 1.5 eq) of 3-amino-1,2-propanediol were mixed and stirred for 1 day. 50 ml of methylene chloride was added to the reaction solution, which was then cooled to 0° C. Then, 1.83 g (5.42 mmol, 1 eq) of dimethyl chloride was added to the reaction solution, followed by stirring. A solution of 3.03 ml (21.68 mmol, 4 eq) of triethylamine in 10 ml of methylene chloride was added dropwise to the reaction solution, followed by stirring at room temperature for 4 hours. Then, the reaction solution was concentrated under reduced pressure and extracted with methylene chloride. The extract was dried with magnesium sulfate and filtered. The filtrate was concentrated under reduced pressure and separated by a column. The separated material was concentrated under reduced pressure and dried in a vacuum to afford 0.92 g (41.9%) of the desired compound.

$^1$H NMR (300 MHz, CDCl$_3$):7.55-7.53 (1H, s), 7.43-7.39 (2H, m), 7.32-7.15 (7H, m), 6.83-6.78 (4H, d), 6.17-6.15 (1H, s), 3.87-3.85 (1H, m), 3.75-3.73 (6H, s), 3.68-3.65 (1H, m), 3.53-3.46 (1H, m), 3.32-3.22 (2H, m), 3.20-3.09 (2H, m), 2.11-2.04 (2H, t), 1.61-1.46 (4H, m), 1.33-1.24 (2H, m)

5-8: Preparation of Compound of Process 8—Amine Deprotection 0.84 g (1.39 mmol, 1 eq) of the process 7 compound and 5 ml of methanol were mixed and stirred. 4.26 ml (27.8 mmol, 20 eq) of ammonia solution (25%) was added dropwise to the mixture, followed by stirring for 1 day. The reaction solution was extracted with methylene chloride. The extract was dried with sodium sulfate and filtered. The filtrate was concentrated under reduced pressure and dried in a vacuum to afford 0.78 g (>100%) of the desired compound.

$^1$H NMR (300 MHz, CDCl$_3$):7.42-7.38 (2H, m), 7.31-7.17 (7H, m), 6.83-6.78 (4H, d), 6.61-6.59 (1H, s), 3.91-3.89 (1H, m), 3.76-3.74 (6H, s), 3.54-3.48 (2H, m), 3.20-3.09 (2H, m), 2.93-2.89 (2H, m), 2.16-2.10 (2H, m), 1.70-1.56 (4H, m), 1.38-1.31 (2H, m)

5-9: Preparation of Compound of Process 9—Amidation ($C_9$-spacer)

0.23 g (0.54 mmol, 1 eq) of the process 4 compound, 0.26 g (0.59 mmol, 1.1 eq) of bis-2-oxo-3-oxazolidinylphosphoric chloride, 0.08 g (0.59 mmol, 1.1 eq) of 1-hydroxybenzotriazole, 0.3 g (0.59 mmol, 1.1 eq) of the process 8 compound, and 100 ml of methylene chloride were mixed and stirred. 0.37 ml (2.69 mmol, 5 eq) of triethylamine was added to the reaction solution, followed by stirring for 15 hours. Then, the reaction solution was concentrated under reduced pressure. The concentrate was extracted with ethyl acetate. The organic layer was dried with sodium sulfate and filtered. The filtrate was concentrated under reduced pressure and separated by a column. The separated material was concentrated under reduced pressure and dried in a vacuum to afford 0.42 g (84.2%) of the desired compound.

$^1$H NMR (300 MHz, CDCl$_3$):8.80-8.78 (2H, d), 7.93-7.90 (2H, d), 7.86-7.83 (1H, d), 7.72-7.70 (2H, d), 7.60-7.58 (1H, s), 7.55-7.52 (1H, d), 7.46-7.38 (2H, m), 7.31-7.17 (7H, m), 6.82-6.78 (4H, d), 6.78-6.75 (2H, d), 6.50-6.44 (1H, t), 6.15-6.13 (1H, s), 4.04-4.02 (3H, s), 4.00-3.98 (3H, s), 3.88-3.86 (1H, m), 3.75-3.73 (8H, m), 3.55-3.21 (4H, m), 3.23-3.07 (4H, m), 2.48-2.46 (2H, t), 2.10-2.04 (2H, t), 1.58-1.42 (4H, m), 1.29-1.15 (5H, m)

5-10: Preparation of Compound of Process 10—Succinylation 0.46 g (0.49 mmol, 1 eq) of the process 9 compound, 0.25 g (2.46 mmol, 5 eq) of succinic anhydride, 0.03 g (0.25 mmol, 0.5 eq) of N,N-dimethylaminopyridine, and 35 ml of pyridine were mixed and stirred. The mixture was heated to 60° C. and stirred for 1 day. Then, the reaction solution was cooled to room temperature and concentrated under reduced pressure. The concentrate was extracted with methylene chloride. The extract was dried with sodium sulfate and filtered. The filtrate was concentrated under reduced pressure and separated by a column. The separated material was concentrated under reduced pressure and dried in a vacuum to afford 0.03 g (6.7%) of the desired compound.

$^1$H NMR (300 MHz, CDCl$_3$):8.77-8.75 (2H, d), 7.90-7.87 (2H, d), 7.83-7.80 (1H, d), 7.73-7.71 (2H, d), 7.59-7.57 (1H, s), 7.53-7.50 (1H, d), 7.48-7.38 (2H, m), 7.32-7.18 (7H, m), 6.84-6.80 (4H, d), 6.80-6.77 (2H, d), 6.40-6.38 (1H, t), 5.93-5.91 (1H, t), 5.24-5.22 (1H, m), 4.08-4.06 (3H, s), 4.04-4.02 (3H, s), 3.91-3.82 (2H, m), 3.79-3.77 (8H, m), 3.50-3.46 (2H, m), 3.29-3.17 (4H, m), 2.72-2.50 (6H, m), 2.05-1.96 (2H, t), 1.64-1.49 (4H, m), 1.36-1.18 (5H, m)

5-11: Preparation of Compound of Process 11—LCAA-CPG Coupling 16.8 g of LCAA-CPG, 1.14 g (1.1 mmol, 1 eq) of the process 10 compound, 0.5 g (1.1 mmol, 1 eq) of bis-2-oxo-3-oxazolidinylphosphoric chloride, 0.15 g (1.1 mmol, 1 eq) of 1-hydroxybenzotriazole, 100 ml of methylene chloride, and 0.6 ml (5.5 mmol, 5 eq) of triethylamine were mixed and stirred at room temperature for 1 day. The reaction solution was filtered and washed with methanol. The filtrate was dried in a vacuum to afford 18.03 g of the desired compound.

5-12: Preparation of Compound of Process 12—Capping 18.03 g of the process 11 compound, 90 ml of pyridine, 3.59 ml (38 mmol) of acetic anhydride, and 18 ml (225 mmol) of 1-methylimidazole were mixed and stirred for 1.5 hours. The reaction solution was filtered and washed with methanol. The filtrate was dried in a vacuum to afford 15.00 g of the desired compound.

$^1$H NMR analysis of the products prepared in the above Preparation Examples indicated that the products had the desired structures.

EXAMPLE 1

Measurement of Emission Intensity Using Oligonucleotide

To examine the emission intensity of the quenchers prepared in the present invention, each of BHQ1, BHQ2, quencher 570, quencher 630 and quencher 640 was bound to the 3' end of 10-mer oligonucleotide (Table 1) as a template strand to synthesize oligonucleotides. The emission intensities of the oligonucleotides were measured in a wavelength range of 200 nm to 1000 nm.

The emission intensities of the quenchers of the present invention were measured in the following manner using Optizen POP (spectrophotometer, Mecasys).

(1) Each of the synthesized quenchers was diluted at a concentration of 100 pmole/ul, and 1 nmole was allowed to react.

(2) As shown in Table 2 below, each quencher was diluted to a final volume of 100 ul, and the fluorescence of each quencher was measured in a wavelength range of 200 nm to 1000 nm using a spectrophotometer.

TABLE 1

| | Nucleotide sequence (5'→ 3') |
|---|---|
| 10mer nucleotide sequence | ACG TCA CGG T |

TABLE 2

| | |
|---|---|
| Quencher (100 pmole/ul) | 10 ul |
| distilled water | To 100 ul |
| Total volume | 100 ul |

The results of the measurement are shown in FIG. 1. As can be seen in FIG. 1, each quencher quenched fluorescence.

EXAMPLE 2

RT-PCR Analysis Using Quencher 570

In order to examine the performance of a probe comprising quencher 570 in RT-PCR, RT-PCR primers and a RT-PCR probe were designed using lambda phage DNA (Bioneer) as a template strand (Table 3).

In order to prepare the probe used in the present invention, the 5' end of 25 mer oligonucleotide was labeled with each of fluorescent FAM, TET, TAMRA, ROX and Texas-Red, and the 3' end was labeled with quencher 570. For a control probe, the 5' end was labeled with each of fluorescent FAM, TET, TAMRA, ROX and Texas-Red, and the 3' end was labeled with BHQ1 and BHQ2.

Real-time quantitative PCR was performed in the following manner using AccuPower DualStar™ RT-PCR PreMix (Bioneer) and Real-Time PCR machine Exicycler (Bioneer).

(1) Lambda DNA (10 ng/ul-10 pg/ul) was diluted serially 10-fold.

(2) As shown in Table 4 below, each sample having a total volume of 20 ul was prepared.

(3) RT-PCR was performed under the conditions shown in Table 5 below.

TABLE 3

| | Nucleotide sequence (5'→ 3') |
|---|---|
| Forward primer | GGA CTG GCT GAT GAA CTT GTT A |
| Reverse primer | GTG GCT GAA ACA GTT GTT GAT T |
| Probe | ATG CAC TGG ATG CAC GTA AAT CCC G |

TABLE 4

| Reaction in one tube | |
|---|---|
| Lambda DNA (10 ng-1 pg) | Each 1 ul |
| Forward primer | 10 pmole/ul |
| Reverse primer | 10 pmole/ul |
| Probe | 10 pmole/ul |
| Distilled water | To 20 ul |
| Total volume | 20 ul |

TABLE 5

| Reaction | Temperature (time) | Number of cycles |
|---|---|---|
| Pre-Denaturing | 95° C. (5 min) | 1 |
| Denaturing | 95° C. (20 sec) | 45 |
| Annealing & Extension | 55° C. (30 sec) | |
| Detention(Scan) | | |

As a result, it could be seen that quencher 570 had excellent quenching performance.

Tables 6 to 10 below show Ct (cycle threshold) values in the above RT-PCR experiments (FIGS. 2 to 6).

The Ct values in Tables 6 to 10 show the number of cycles measured while increasing the DNA concentration by 10-fold. As can be seen in the Tables, the use of the quencher of the present invention showed a difference of about 3.3 Ct at each DNA concentration, indicating that real-time PCR is easily performed when using the quencher of the present invention. Thus, it can be seen that the quenchers of the present invention have quenching ability comparable to the conventional quencher BHQ.

TABLE 6

Comparison of Ct between quencher 570/FAM and BHQ1/FAM

| FAM | | Quencher batch1 | Quencher batch1 | BHQ1 |
|---|---|---|---|---|
| 1 × 10^7 copies/rxn | 1 | 18.03 | 18.31 | 18.46 |
| | 2 | 18.09 | 18.12 | 18.22 |
| | Average | 18.06 | 18.215 | 18.34 |
| 1 × 10^6 copies/rxn | 1 | 21.02 | 21.19 | 21.15 |
| | 2 | 20.72 | 20.95 | 21.10 |
| | Average | 20.87 | 21.07 | 21.13 |
| 1 × 10^5 copies/rxn | 1 | 25.14 | 25.19 | 25.17 |
| | 2 | 24.86 | 25.07 | 25.00 |
| | Average | 25 | 25.13 | 25.09 |
| 1 × 10^4 copies/rxn | 1 | 28.52 | 28.61 | 28.69 |
| | 2 | 28.38 | 28.55 | 28.17 |
| | Average | 28.45 | 28.58 | 28.43 |

TABLE 7

Comparison of Ct between quencher 570/TET and BHQ1/TET

| TET | | Quencher batch1 | Quencher batch1 | BHQ1 |
|---|---|---|---|---|
| $1 \times 10^7$ copies/rxn | 1 | 18.25 | 18.56 | 18.27 |
| | 2 | 18.09 | 17.97 | 18.05 |
| | Average | 18.17 | 18.265 | 18.16 |
| $1 \times 10^6$ copies/rxn | 1 | 21.03 | 21.19 | 21.12 |
| | 2 | 21 | 20.87 | 21.03 |
| | Average | 21.015 | 21.03 | 21.08 |
| $1 \times 10^5$ copies/rxn | 1 | 25.01 | 24.81 | 25.18 |
| | 2 | 24.65 | 24.59 | 24.72 |
| | Average | 24.83 | 24.7 | 24.95 |
| $1 \times 10^4$ copies/rxn | 1 | 28.6 | 28.67 | 28.52 |
| | 2 | 28.36 | 28.28 | 28.30 |
| | Average | 28.48 | 28.475 | 28.41 |

TABLE 8

Comparison of Ct between quencher 570/TAMRA and BHQ1/TAMRA

| TAMRA | | BHQ1 | Quencher570 |
|---|---|---|---|
| $1 \times 10^7$ copies/rxn | 1 | 23.4 | 23.47 |
| | 2 | 23.37 | 23.14 |
| | Average | 23.39 | 23.31 |
| $1 \times 10^6$ copies/rxn | 1 | 26.5 | 26.7 |
| | 2 | 26.68 | 26.36 |
| | Average | 26.59 | 26.53 |
| $1 \times 10^5$ copies/rxn | 1 | 29.55 | 29.61 |
| | 2 | 29.36 | 29.28 |
| | Average | 29.46 | 29.46 |
| $1 \times 10^4$ copies/rxn | 1 | 31.91 | 32.06 |
| | 2 | 31.96 | 31.84 |
| | Average | 31.94 | 31.95 |

TABLE 9

Comparison of Ct between quencher 570/ROX and BHQ2/ROX

| ROX | | Quencher batch1 | Quencher batch1 | BHQ2 |
|---|---|---|---|---|
| $1 \times 10^7$ copies/rxn | 1 | 17.85 | 17.78 | 18.01 |
| | 2 | 17.9 | 17.56 | 18.01 |
| | Average | 17.875 | 17.67 | 18.01 |
| $1 \times 10^6$ copies/rxn | 1 | 20.9 | 20.94 | 21.23 |
| | 2 | 21.03 | 21.08 | 20.98 |
| | Average | 20.965 | 21.01 | 21.11 |
| $1 \times 10^5$ copies/rxn | 1 | 25.2 | 24.5 | 24.53 |
| | 2 | 24.36 | 24.3 | 24.37 |
| | Average | 24.78 | 24.405 | 24.45 |
| $1 \times 10^4$ copies/rxn | 1 | 27.83 | 27.89 | 27.83 |
| | 2 | 27.38 | 27.78 | 27.52 |
| | Average | 27.605 | 27.835 | 27.68 |

TABLE 10

Comparison of Ct between quencher 570/Texas-Red and BHQ2/Texas-Red

| Texas-Red | | Quencher batch1 | Quencher batch1 | BHQ2 |
|---|---|---|---|---|
| $1 \times 10^7$ copies/rxn | 1 | 17.83 | 17.89 | 17.82 |
| | 2 | 17.87 | 17.76 | 17.46 |
| | Average | 17.85 | 17.825 | 17.64 |
| $1 \times 10^6$ copies/rxn | 1 | 20.88 | 21.09 | 20.92 |
| | 2 | 21.23 | 21.03 | 20.80 |
| | Average | 21.055 | 21.06 | 20.86 |

TABLE 10-continued

Comparison of Ct between quencher 570/Texas-Red and BHQ2/Texas-Red

| Texas-Red | | Quencher batch1 | Quencher batch1 | BHQ2 |
|---|---|---|---|---|
| $1 \times 10^5$ copies/rxn | 1 | 24.19 | 23.36 | 24.13 |
| | 2 | 24.2 | 24.3 | 24.17 |
| | Average | 24.195 | 23.88 | 24.15 |
| $1 \times 10^4$ copies/rxn | 1 | 27.76 | 27.64 | 27.63 |
| | 2 | 27.47 | 27.77 | 27.26 |
| | Average | 27.615 | 27.705 | 27.45 |

The present invention can be used in various applications in the biological and chemical fields.

Although the preferred embodiments of the present invention have been described for illustrative purposes, the present invention is not limited thereto and various modifications, additions and substitutions can be made to the present invention by those skilled in the art, without departing from the scope and spirit of the invention as disclosed in the accompanying claims.

The invention claimed is:

1. A quencher comprising a compound represented by the following formula 1:

$$A^1-N=N-A^2-N=N-A^3 \qquad \text{Formula 1}$$

wherein
$A^1$ has a structure of the following formula 2;
$A^2$ has a structure of the following formula 4; and
$A^3$ has a structure of the following formula 5,

Formula 2 wherein
$Z^1$ to $Z^4$ are $CR^1$
$R^1$ is hydrogen or a nitro group;
$X^1$ is $CH_2$, NH, sulfur or oxygen; and
$X^2$ is CH or nitrogen,

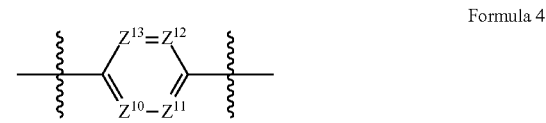

Formula 4 wherein
$Z^{10}$ to $Z^{13}$ are $CR^3$;
$R^3$ is hydrogen, a hydroxyl group, a $C_1$-$C_{10}$ alkoxy group $NR^{11}R^{12}$, or a $C_1$-$C_{10}$ alkyl group, with the proviso that all $CR^3$ are not simultaneously hydrogen;

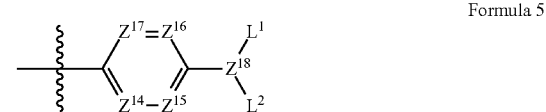

Formula 5 wherein,
$Z^{14}$ to $Z^{17}$ are $CR^4$;
$R^4$ is hydrogen or a $C_1$-$C_{10}$ alkyl group;
$Z^{18}$ is CH or nitrogen; and
$L^1$ and $L^2$ are each independently hydrogen, a $C_1$-$C_{30}$ alkyl group, a hydroxy-substituted $C_1$-$C_{30}$ alkyl group, a $C_1$-$C_{30}$ carboxyl group or a $C_1$-$C_{30}$ carbonyloxy-substituted $C_1$-$C_{30}$ alkyl group, or $A^1$ has a structure of the following formula 3;
$A^2$ has a structure of the following formula 4; and
$A^3$ has a structure of the following formula 5, Formula 3

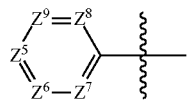

wherein
$Z^5$ is nitrogen and $Z^6$ to $Z^9$ are each independently $CR^2$;
$R^2$ is hydrogen Formula 4

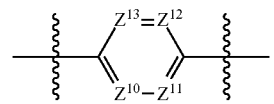

wherein
$Z^{10}$ to $Z^{13}$ are $CR^3$;
$R^3$ is hydrogen, a hydroxyl group or a $C_1$-$C_{10}$ alkoxy group or a $C_1$-$C_{10}$ alkyl group Formula 5

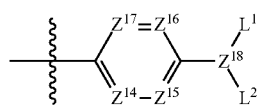

wherein,
$Z^{14}$ to $Z^{17}$ are $CR^4$;
$R^4$ is hydrogen or a $C_1$-$C_{10}$ alkyl group
$Z^{18}$ is CH or nitrogen; and
$L^1$ and $L^2$ are each independently hydrogen, a $C_1$-$C_{30}$ alkyl group a hydroxy-substituted $C_1$-$C_{30}$ alkyl group, a $C_1$-$C_{30}$ carboxyl group or a $C_1$-$C_{30}$ carbonyloxy-substituted $C_1$-$C_{30}$ alkyl group.

2. The quencher of claim 1, which comprises a compound selected from compounds represented by the following formulas 6 and 7:

Formula 6

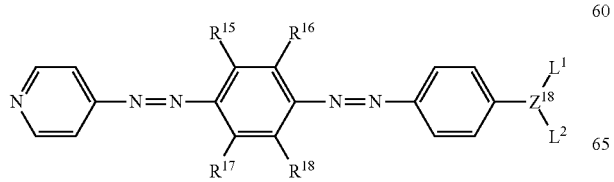

Formula 7

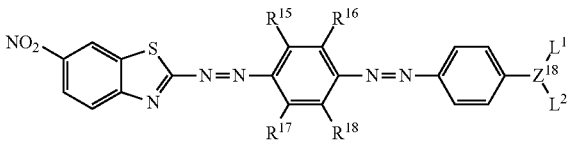

wherein
$Z^{18}$ is CH or nitrogen;
$L^1$ and $L^2$ are each independently hydrogen, a $C_1$-$C_{30}$ alkyl group, a hydroxy-substituted $C_1$-$C_{30}$ alkyl group, a $C_1$-$C_{30}$ carboxyl group, or a $C_1$-$C_{30}$ carbonyloxy-substituted $C_1$-$C_{30}$ alkyl group; and
$R^{15}$ to $R^{18}$ are each independently H, a $C_1$-$C_{10}$ alkoxy group, or a $C_1$-$C_{10}$ alkyl group, with the proviso that in formula 7 all R15 to R18 are not simultaneously H.

3. The quencher of claim 1, which comprises any one selected from among compounds represented by the following formulas 8 to 12:

Formula 8

Formula 9

Formula 10

Formula 11

Formula 12

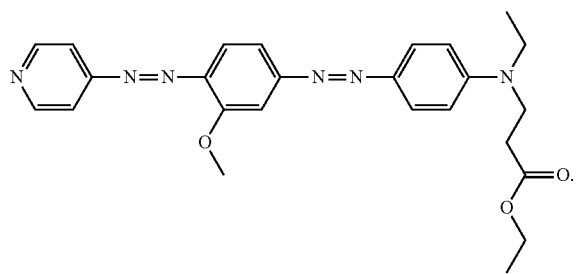

4. The quencher of claim 1, further comprising a cleavable support linked by any one linker selected from among L1 or L2, and a hydroxyl group protected with DMT (4,4'-dimethoxytrityl group) or its derivative as a protecting group.

5. The quencher of claim 4, which further comprises any one selected from among compounds represented by the following formulas 13 to 17 for oligomer synthesis:

Formula 13

Formula 14

Formula 15

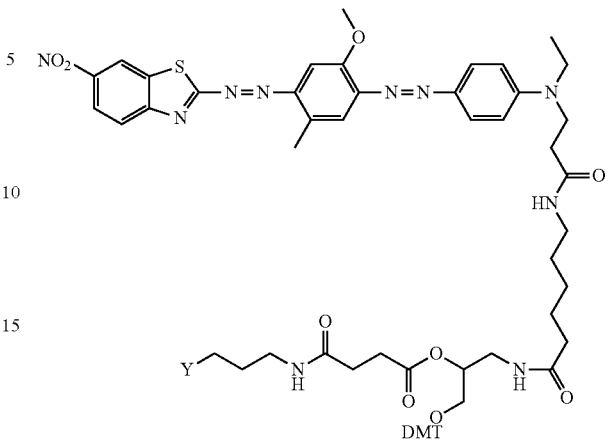

Formula 16

Formula 17 wherein Y is a support.

6. An oligonucleotide comprising the quencher of any one of claim 1.

7. The oligonucleotide of claim 6, which comprises a probe.

8. A composition for detecting a nucleic acid, comprising the oligonucleotide of claim 6.

9. The oligonucleotide of claim 7, wherein the probe comprises a fluorophore that is a reporter.

10. The oligonucleotide of claim 9, wherein the fluorophore comprises one or more selected from the group consisting of coumarin, fluorescein, rhodamine, BODIPY, cyanine, and derivatives thereof.

11. An azo compound selected from compounds represented by the following formulas 6 and 7:

Formula 6

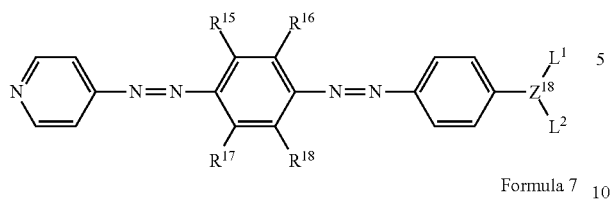

Formula 7

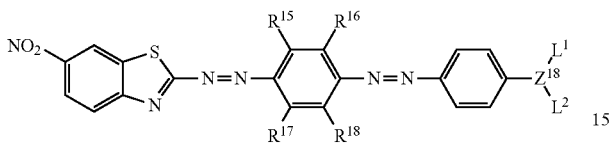

wherein $Z^{18}$ is CH or nitrogen;

$L^1$ and $L^2$ are each independently hydrogen, a $C_1$-$C_{30}$ alkyl group, a hydroxy-substituted $C_1$-$C_{30}$ alkyl group, a $C_1$-$C_{30}$ carboxyl group or a $C_1$-$C_{30}$ carbonyloxy-substituted $C_1$-$C_{30}$ alkyl group; and $R^{15}$ to $R^{18}$ are each independently H, a $C_1$-$C_{10}$ alkoxy group, or a $C_1$-$C_{10}$ alkyl group, with the proviso that in formula 7 all R15 to R18 are not simultaneously H.

12. A method for preparing the azo compound represented by the following formula 6 of claim 11, the method comprising the steps of:

subjecting a compound of the following formula 6a to an azo coupling reaction with a compound of the following formula 6b to obtain a compound of the following formula 6c; and subjecting the obtained compound of formula 6c to an azo coupling reaction with a compound of the following formula 6d to obtain a compound of formula 6:

Formula 6a

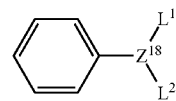

Formula 6b

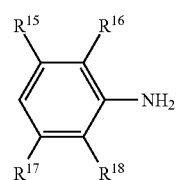

Formula 6c

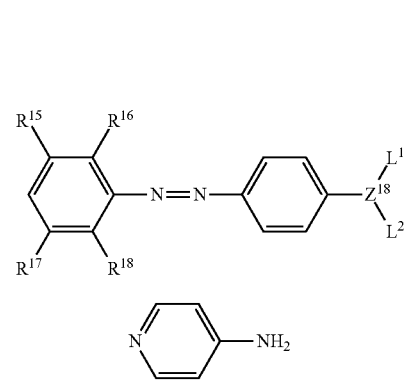

Formula 6d

-continued

Formula 6

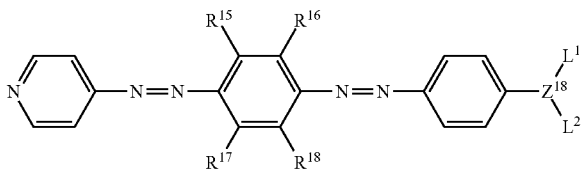

wherein $Z^{18}$ is CH or nitrogen;

$L^1$ and $L^2$ are each independently hydrogen, a $C_1$-$C_{30}$ alkyl group, a hydroxy-substituted $C_1$-$C_{30}$ alkyl group, a $C_1$-$C_{30}$ carboxyl group or a $C_1$-$C_{30}$ carbonyloxy-substituted $C_1$-$C_{30}$ alkyl group; and $R^{15}$ to $R^{18}$ are each independently H, a $C_1$-$C_{10}$ alkoxy group, or a $C_1$-$C_{10}$ alkyl group.

13. A method for preparing the azo compound represented by the following formula 7 of claim 11, wherein the method comprising the steps of:

subjecting a compound of the following formula 6a to an azo coupling reaction with the compound of the following formula 6b to obtain a compound of the following formula 6c; and subjecting the obtained compound of formula 6c to an azo coupling reaction with a compound of the following formula 7a to obtain a compound of the following formula 7:

Formula 6a

Formula 6b

Formula 6c

Formula 7a

Formula 7 wherein $Z^{18}$ is CH or nitrogen;

$L^1$ and $L^2$ are each independently hydrogen, a $C_1$-$C_{30}$ alkyl group, a hydroxy-substituted $C_1$-$C_{30}$ alkyl group, a $C_1$-$C_{30}$ carboxyl group or a $C_1$-$C_{30}$ carbonyloxy-substituted $C_1$-$C_{30}$ alkyl group; and $R^{15}$ to $R^{18}$ are each independently H, a $C_1$-$C_{10}$ alkoxy group, or a $C_1$-$C_{10}$ alkyl group.

14. The quencher of claim 1, wherein $A^1$ has the structure of formula 3, $A^2$ has the structure of formula 4, and $A^3$ has the structure of formula 5, wherein $Z^{10}$ to $Z^{13}$ are $CR^3$ wherein $R^3$ are each independently hydrogen, methyl, or methoxy, $L^1$ is ethyl, and $L^2$ is $HOC(O)(CH_2)_2$.

15. The quencher of claim 1, wherein $A^1$ has the structure of formula 2, $A^2$ has the structure of formula 4, and $A^3$ has the structure of formula 5, wherein $Z^1$, $Z^3$, and $Z^4$ are CH and $Z^2$ is $CNO_2$, $X^1$ is sulfur, $X^2$ is nitrogen, $Z^{10}$ to $Z^{13}$ are $CR^3$ wherein $R^3$ are each independently hydrogen, methyl, or methoxy, $L^1$ is ethyl or $CH_3C(O)O(CH_2)_2$, and $L^2$ is $HOC(O)(CH_2)_2$ or $HO(CH_2)_3$.

* * * * *

UNITED STATES PATENT AND TRADEMARK OFFICE
CERTIFICATE OF CORRECTION

PATENT NO. : 10,167,391 B2  Page 1 of 1
APPLICATION NO. : 14/417510
DATED : January 1, 2019
INVENTOR(S) : Sun Gi Kim It is certified that error appears in the above-identified patent and that said Letters Patent is hereby corrected as shown below:

On the Title Page

Item [56]:

FOREIGN PATENT DOCUMENTS, Line 17, for "WO 2010-106242 A", should be deleted.

OTHER PUBLICATIONS, Line 5, "Zhumal" should read -- Zhurnal --.

In the Specification

Columns 23-26, in the chemical formula of the reaction of the lower portion of Columns 23 and 24, and in the reaction product at the upper portion of Columns 25 and 26, the substituent "OTMD" should read -- ODMT --, so that the formula are specified as follows:

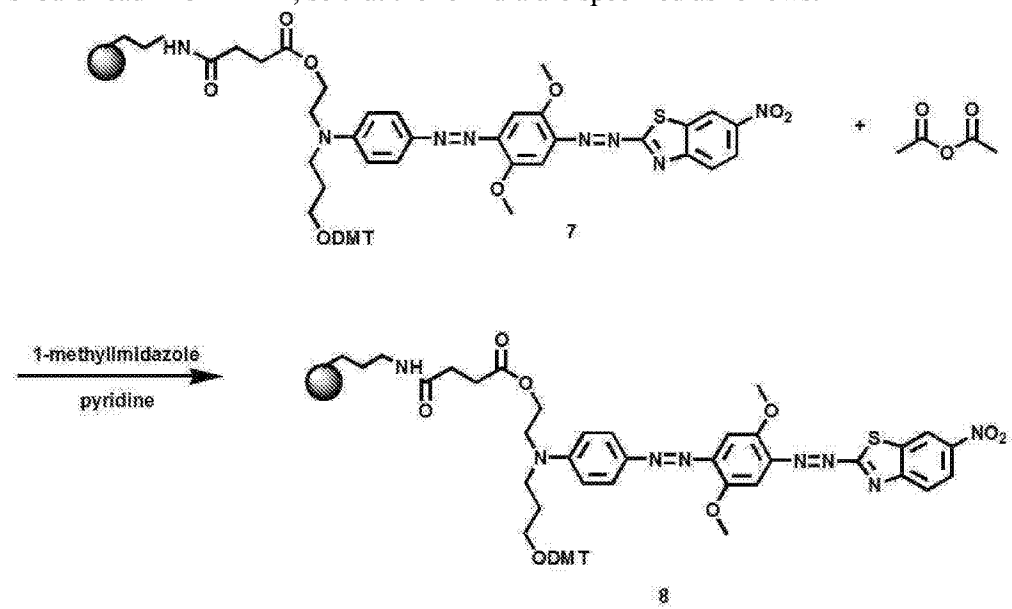

Signed and Sealed this
Second Day of April, 2019

Andrei Iancu
*Director of the United States Patent and Trademark Office*